United States Patent [19]

Inouye et al.

[11] Patent Number: 5,272,065
[45] Date of Patent: Dec. 21, 1993

[54] REGULATION OF GENE EXPRESSION BY EMPLOYING TRANSLATIONAL INHIBITION OF MRNA UTILIZING INTERFERING COMPLEMENTARY MRNA

[75] Inventors: Masayori Inouye, Bridgewater, N.J.; Takeshi Mizuno, Meiko, Japan; Mei-Yin Chou, N. Plainfield, N.J.

[73] Assignee: Research Foundation of State University of New York, Albany, N.Y.

[21] Appl. No.: 542,209

[22] Filed: Jun. 21, 1990

Related U.S. Application Data

[63] Continuation of Ser. No. 436,598, Nov. 15, 1989, which is a continuation-in-part of Ser. No. 300,741, Jan. 23, 1989, abandoned, and Ser. No. 228,852, Aug. 3, 1988, abandoned, which is a continuation of Ser. No. 543,528, Oct. 20, 1983, abandoned, said Ser. No. 300,741, is a continuation of Ser. No. 585,282, Mar. 1, 1984, abandoned, which is a continuation-in-part of Ser. No. 543,528, Mar. 1, 1984.

[51] Int. Cl.$^5$ .................. C12P 19/34; C07H 15/12; A61K 48/00
[52] U.S. Cl. .................. 435/91.1; 435/240.2; 435/320.1; 435/172.3; 435/252.3; 435/252.33; 514/44; 536/24.1; 935/2; 935/3; 935/6; 935/33; 935/36; 935/55; 935/62; 935/66; 800/2
[58] Field of Search .................. 435/172.3, 235, 320.1, 435/172.1, 240.2, 252.3, 91; 514/44; 536/27; 424/93; 935/33, 35, 36, 37, 4

[56] References Cited

U.S. PATENT DOCUMENTS

| | | | |
|---|---|---|---|
| 4,469,893 | 9/1984 | Ts'o et al. | 536/27 |
| 4,503,151 | 3/1985 | Paddock et al. | 435/69.1 |
| 4,511,713 | 4/1985 | Miller et al. | 536/27 |
| 4,740,463 | 4/1988 | Weinberg et al. | 435/172.3 |
| 4,801,540 | 1/1989 | Hiatt et al. | 435/240.4 |
| 4,912,040 | 3/1990 | Kaufman et al. | 435/69.6 |
| 5,023,243 | 6/1991 | Tullis | 514/44 |

FOREIGN PATENT DOCUMENTS

WO83/01451 4/1983 World Int. Prop. O. .

OTHER PUBLICATIONS

Wong et al., 1982, Biochem. Biophys. Res. Commun. 107, 584–587.
Simons et al., 1983, Cell 34, 683–691.
Chilton, M. D., 1983, Sci. Am., 248, 50–59.
Weinstein et al. (eds.) 083. in: *Genes and Proteins in Oncogenesis*, Academic Press, N.Y., pp. 253–265.
Biol. Abs. 73, 3743, Abs. No. 36372, Naora et al.
Herskowitz, *Principles of Genetics* (2nd Ed.) MacMillan Publishing Co., NY, pp. 56 and 492–493 (1977).
Kolter et al., "Attenuation in Amino Acid Biosynthetic Operons" *Ann. Rev. Genet.* 16:113–134 (1982).
Light et al., "Post-transcriptional control of expression of the repA gene of plasmid R1 mediated by a small RNA molecule." *EMBO J.* 2:93–98 (1983).
Saito et al., "Processing of mRNA by Ribonuclease III Regulates Expression of Gene 1.2 of Bacterophage T7", *Cell* 27:533–542 (1981).
Light et al., "The Sites of Action of the Two Copy Number Control Functions of Plasmid R1", *Mol. Gen. Genet.* 187:486–493 (1982).
Tomizawa et al., "Plasmid ColE1 incompatability determined by interaction of RNA I with primer transcript", *Proc. Natl. Acad. Sci. USA* 78:6096–6100 (1981).
Metzler, D. E., "Nucleic Acids" in Biochemistry. *The Chemical Reactions of Living Cells*. Academic Press New York, N.Y., p. 103 (1977).
Eisenberg et al., Chapter 4: "Free Energy and Equilibrium" in *Physical Chemistry with Applications to the Life Sciences*. Benjamin/Cummings Publ. Co., Menlo Park, CA, pp. 155–158 and Table inside back cover (1979).
(List continued on next page.)

*Primary Examiner*—Christopher S. F. Low
*Attorney, Agent, or Firm*—Eugene Moroz; William S. Feiler; Mary J. Morry

[57] ABSTRACT

Gene expression in a cell can be regulated or inhibited by incorporating into or associating with the genetic material of the cell a non-native nucleic acid sequence which is transcribed to produce an mRNA which is complementary to and capable of binding to the mRNA produced by the genetic material of said cell.

147 Claims, 8 Drawing Sheets

OTHER PUBLICATIONS

Som and Tomizawa, "Regulatory regions of ColE1 that are involved in determination of plasmid copy number", *Proc. Natl. Acad. Sci. USA*, 80:3232–3236 (1983).

Stryer, "Biosynthesis of Nucleotides" in *Biochemistry*, W. H. Freeman & Co., S. F., pp. 528–531 (1975).

Zimmer et al., "Genome Distribution of Adenovirus Total and Self-Complementary Nuclear RNA at Early Times", *Virology* 111:301–311 (1981).

Izant et al., "Constitutive and Conditional Suppression of Exogenous and Endogenous Genes by Anti-Sense RNA", *Science* 229:345–52 (1985).

Nordstrom, "Antisense RNA", *Trends in Biochem. Sci.* 10 (6): 232 (1985).

Izant et al., "Inhibition of Thymidine Kinase Gene Expression by Anti-Sense RNA: A Molecular Approach to Genetic Analysis", *Cell* 36:1007–15 (1984).

Stephenson et al., "Inhibition of Rous sarcoma viral RNA translation by a specific oligodeoxyribonucleotide", *Proc. Natl. Acad. Sci. USA* 75:285–88 (1978).

Zamecnik et al., "Inhibition of Rous sarcoma virus replication and cell transformation by a specific oligodeoxynucleotide", *Proc. Natl. Acad. Sci. USA* 75:280–84 (1978).

Maniatis et al., *Molecular Cloning, A Laboratory Manual*, Cold Spring Harbor Laboratory, pp. 211–246 and 405–410 (1982).

Fraley et al., "Expression of bacterial genes in plant cells", *Proc. Natl. Acad. Sci. USA* 80:4803–4807 (1983).

Melton, "Injected anti-sense RNAs specifically block messenger RNA translation in vivo", *Proc. Natl. Acad. Sci. USA* 82:144–148 (1985).

Kim & Wold, "Stable reduction of thymidine kinase activity in cells expressing high levels of anti-sense RNA", *Cell* 42:129–138 (1985).

Crowley et al., "Phenocopy of Discoidin I-Minus Mutants by Antisense Transformation in Dictyostelium", *Cell* 43:633–641 (1985).

Hirashima et al., "Engineering of the mRNA-Interfering complementary RNA immune system against viral infection", *Proc. Natl. Acad. Sci. USA* 83:7726–7730 (1986).

Ecker et al., "Inhibition of gene expression in plant cells by expression of antisense RNA", *Proc. Natl. Acad. Sci. USA* 83:5372–5376 (1986).

Rosenberg et al., "Production of phenocopies by Krüppel antisense RNA injection into Drosophila embryos", *Nature* 313:703–706 (1985).

McGarry et al., "Inhibition of heat shock protein synthesis by heat-inducible antisense RNA", *Proc. Natl. Acad. Sci. USA* 83:399–403 (1986).

Holt et al., "Inducible production of c-fos antisense RNA inhibits 3T3 cell proliferation", *Proc. Natl. Acad. Sci. USA* 83:4794–4798 (1986).

Ellison et al., "Thermal Regulation of $\beta$-Galactosidase Synthesis Using Anti-sense RNA Directed against the Coding Portion of the mRNA", *J. Biol. Chem.* 260:9085–9087 (1985).

Stougaard et al., "Vertical Dye-Buoyant Density Gradients for Rapid Analysis and Preparation of Plasmid DNA", *Anal. Biochem.* 118:191–193 (1981).

Stougaard et al., "RNAs involved in copy-number control and incompatibility of plasmid R1", *Proc. Natl. Acad. Sci. USA* 78:6008–6012 (1981).

Zipser, D., "Polarity and Translational Punctuation" in Beckwith, J. R. and Zipser, D. (eds) *The Lactose Operon*, Cold Spring Harbor Lab Press, N.Y., pp. 221–232 (1970).

Cesarani et al., "Control of ColE1 DNA replication: The rop gene product negatively affects transcription from the replication primer promoter", *Proc. Natl. Acad. Sci. USA* 79:6313–17 (1982).

Tomizawa et al., "Control of ColE1 Plasmid Replication: Enhancement of Binding of RNA I to the Primer Transcript by the Rom Protein", *Cell* 38:871–878 (1984).

Cesareni et al., "Control of pMB1 replication: inhibition of primer formation by Rop requires RNA1", *Embo J.* 3:1365–69 (1984).

Schell et al., "Gene Vectors for Higher Plants", in *Genetic Engineering: Applications to Agriculture*, pp. 200–202, Beltsville Symposia in Agricultural Research (L. D. Owens ed.) (1983).

Lewin, *Genes*, pp. 165–166, pp. 174–194, pp. 310–311 (First Ed.) (1983).

Lewin, *Genes*, pp. 50–52, pp. 553–560 (First Ed.) (1983).

Green et al., "The role of antisense RNA in gene regulation", *Ann. Rev. Biochem.* 55:569–97 (1986).

Mizuno et al., "A unique mechanism regulating gene expression: Translational inhibition by a complemen-

OTHER PUBLICATIONS tary RNA transcript (mic RNA)", *Proc. Natl. Acad. Sci. USA* 81:1966–1970 (1984).

Coleman et al., "The Use of RNAs Complementary to Specific MRNAs to Regulate the Expression of Individual Bacterial Genes", *Cell* 37:429–436 (1984).

Tomizawa et al. "The Importance of RNA Secondary Structure in ColE1 Primer Formation" *Cell* 31:575–583 (1982).

Boyer et al. *Genetic Engineering* Elsevier/North-Holland Biomedical Press pp. 25, 26 and 163 (1978).

Mizuno et al. "Regulation of Gene Expression by a Small RNA Transcript (micRNA) in *Escherichia coli* K-12" *Proc. Jap. Acad.* 59(B): 335–338 (1983).

La Porte "Antisense RNA: a new mechanism for the control of gene expression" *Trends in Biochem. Sci.* 9:463 (1984).

Daniels and Alberty *Physical Chemistry*, John Wiley & Sons, 4th ed. pp. 156, 170 (1975).

Salser "Globin mRNA Sequences: Analysis of Bas Pairing and Evolutionary Implications" *Cold Spring Harbor Symp. Quant. Biol.* 121:985–1002 (1977).

Fresco "A New Spectroscopic Approach to the Determination of Helical Secondary Structure in Ribonucleic Acids" *Cold Spring Harbor Symp. Quant. Biol.* 28:83–90 (1963).

Fresco, et al. "Some Molecular Details of the Secondary Structure of Ribonucleic Acid" *Nature* 188:98–101 (1960).

Paterson et al. "Structural gene identification and mapping by DNA:mRNA hybrid-arrested cell-free translation" *Chemical Abstract* 87:196,773t (1977).

Paterson et al. "Structural gene identification and mapping by DNA:mRNA hybrid-arrested cell-free translation" *Proc. Natl. Acad. Sci. USA* 74:4370–4374 (1977).

Hastie et al. "Analysis of mRNA populations by cDNA-mRNA hybrid-mediated inhibition of cell ∝ free protein synthesis" *Proc. Natl. Acad. Sci. USA* 75:1217–1221.

Inglis et al. "Polypeptides Specified by the Influenze Virus Genome, 2. Assignment of Protein Coding Functions to Individual Genome Segments by in vitro Translation", *Virology* 78:522–536 (1977).

Miller et al., "Synthesis of Oligodeoxyribonucleotide Ethyl Phosphotriesters and Their Specific Complex Formation with Transfer Ribonucleic Acid", *Biochem.* 3:4887–4895 (1974).

Barrett et al., "Inhibitory Effect of Complex Formation with Oligonucleotide Ethyl Phosphotriesters on Transfer Ribonucleic Acid Aminoacylation", *Biochem.* 13:4897–4906 (1974).

Miller et al., "Effects of a Trinucleotide Ethyl Phosphtriester, $G^mp(Et)G^mp(Et)U$, on Mammalian Cells in Culture", *Biochem.* 16:1988–1996 (1977).

Miller et al., "Nonionic Nucleic Acid Analogues. Synthesis and Characterization of Dideoxyribonucleoside Methylphosponates" *Biochem.* 18:5134–5143 (1979).

Miller et al., "Biochemical and Biological Effects of Nonionic Nucleic Acid Methylphosphonates", *Biochem.* 20:1876–1880 (1981).

Narang et al., "Oligonucleotides Containing Phosphotriester Internucleotidic Groups as Novel Substrates for Polynucleotide Enzymes", *Can. J. Biochem.* 53:392–394 (1974).

Pluskal et al., "Isolation of an Oligonucleotide, A Potent Inhibitor of Eukaryotic and Viral Messenger Ribonucleic Acid Translation, from Chick Embryonic Muscle", Biochem. Soc. Trans., 583rd Meeting, Cambridge, 7:1091–1093 (1979).

Summerton et al., "Intracellular Inactivation of Specific Nucleotide Sequences: A General Approach to the Treatment of Viral Diseases and Virally-mediated Cancers", *J. Theor. Biol.* 78:77–99 (1979).

Stebbing et al., "The Design of Antiviral Agents Based on Strategic Sequences in Viral RNA and Antiviral Effects of Single Stranded Polynucleotides", *Pharm. Therap.* 6:291–332 (1979).

Stebbing et al., "Cellular Uptake and In Vivo Fate of Polynucleotides" *Cell. Biol. International Reports* 3:485–502 (1979).

Merril, et al., "*E. coli* gal Operon Proteins Made After Prophage Lambda Induction", *J. Bact.* 147:875–887 (1981).

FIG.1a
[pMY111]
↓ HpaI digestion
↓ XbaI Linker
↓ Ligation
[pMY100]
↓ SalI digestion
↓ Ligation
[pMY150]
↓ BglII digestion
↓ Bal 31 digestion
↓ XbaI Linker
↓ Ligation
[pCX28]
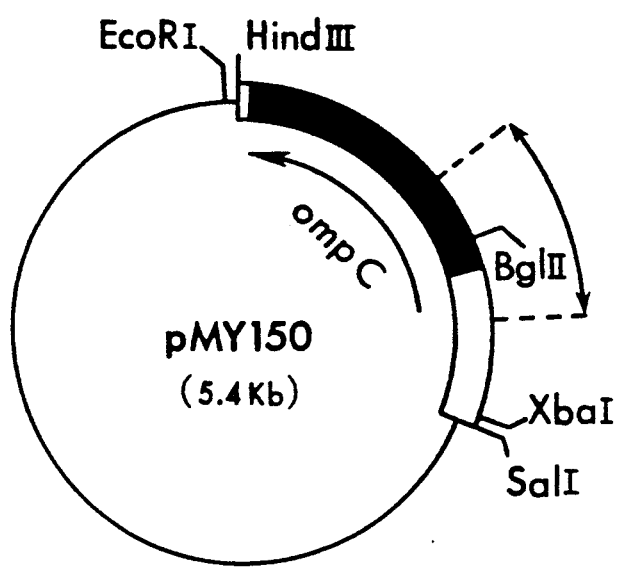
FIG.1b
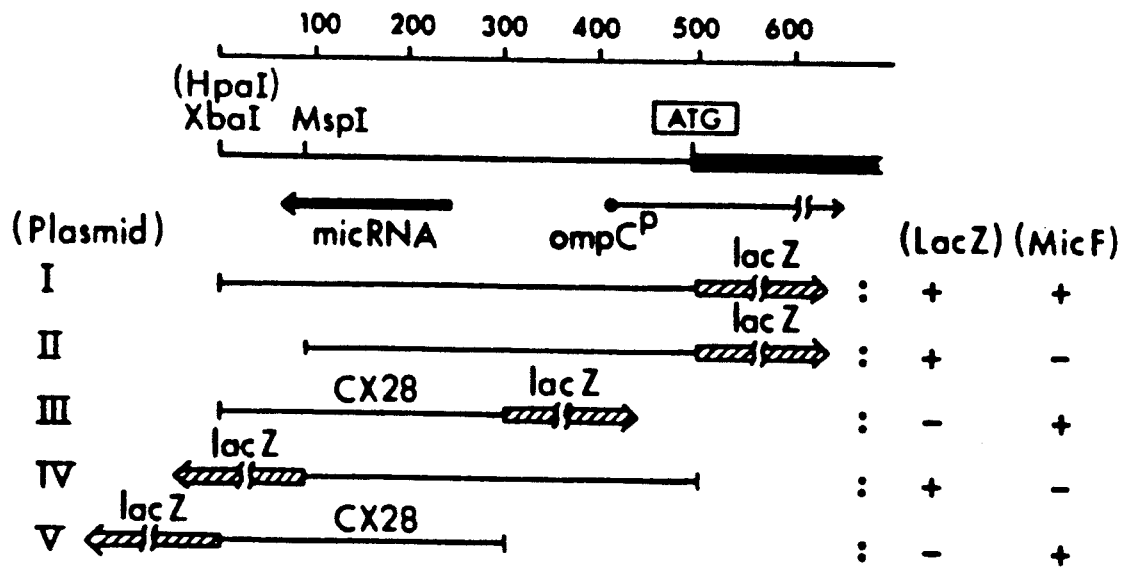
FIG.1c

FIG. 4

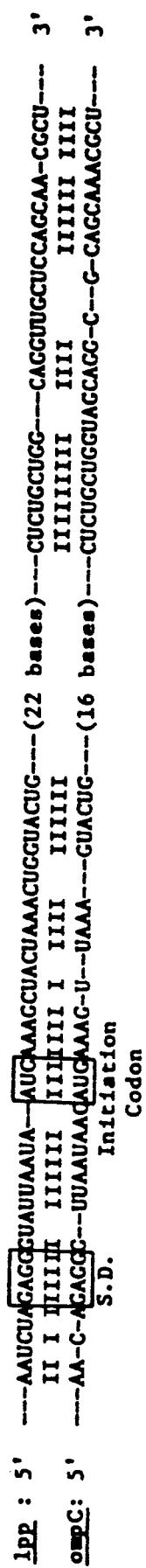

REGULATION OF GENE EXPRESSION BY EMPLOYING TRANSLATIONAL INHIBITION OF MRNA UTILIZING INTERFERING COMPLEMENTARY MRNA

This invention was made with Government support under Grant no. R01-GM-19043 awarded by National Science Foundation. The Government has certain rights in the invention.

REFERENCE TO RELATED APPLICATIONS

This application is a continuation of U.S. patent application Ser. No. 07/436,598, filed Nov. 15, 1989, which is a continuation-in-part of copending coassigned U.S. patent application Ser. No. 07/300,741, filed Jan. 23, 1989, now abandoned, and U.S. patent application Ser. No. 07/228,852, filed Aug. 3, 1988, now abandoned. Application Ser. No. 07/300,741, now abandoned, is in turn a continuation application of U.S. patent application Ser. No. 06/585,282 filed Mar. 1, 1984, now abandoned, which is in turn a continuation-in-part application of U.S. patent application Ser. No. 06/543,528, filed Oct. 20, 1983, now abandoned. Application Ser. No. 07/228,852, now abandoned, is a continuation application of application Ser. No. 06/543,528, filed Oct. 20, 1983, now abandoned.

BACKGROUND OF THE INVENTION

Regulatory control of gene expression has received special attention by scientists. In special circumstances, gene expression has been achieved by employing recombinant DNA as well as other techniques.

For example, in the PCT Patent Application WO 83/01451, published Apr. 23, 1983, there is disclosed a technique employing an oligonucleotide, preferably in phosphotriester form having a base sequence substantially complementary to a portion of messenger ribonucleic acid (mRNA) coding for a biological component of an organism. This oligonucleotide is introduced into the organism and, due to the complementary relationship between the oligonucleotide and the messenger ribonucleotide, the two components hybridize under appropriate conditions to control or inhibit synthesis of the organism s biological component coded for by the messenger ribonucleotide. If the biological component is vital to the organism s viability, then the oligonucleotide could act as an antibiotic. A related technique for the regulation of gene expression in an organism is described in Simons, et al., "Translational Control of IS10 Transposition", Cell 34, 683-691 (1983). The disclosures of the above-identified publications are herein incorporated and made part of this disclosure.

In U.S. patent application Ser. No. 543,528 filed Oct. 20, 1983 of which this application is in turn a continuation-in-part, gene expression is regulated, inhibited and/or controlled by incorporating in or along with the genetic material of the organism, DNA which is transcribed to produce an mRNA having at least a portion complementary to or capable of hybridizing with an mRNA of said organism, such that upon binding or hybridizing to the mRNA, the translation of the mRNA is inhibited and/or prevented. Consequently, production of the protein coded for by the mRNA is precluded. In the instance here, because the mRNA codes for a protein vital to the growth of the organism, the organism becomes disabled. It is also disclosed that this technique for regulating or inhibiting gene expression is applicable to both prokaryotic and eukaryotic organisms, including yeast.

As indicated hereinabove, it is known that the expression of certain genes can be regulated at the level of transcription. Transcriptional regulation is carried out either negatively (repressors) or positively (activators) by a protein factor.

It is also known that certain specific protein factors regulate translation of specific mRNAs As indicated hereinabove, it has become evident that RNAs are involved in regulating the expression of specific genes and it has been reported that a small mRNA transcript of 174 bases is Produced, upon growing Escherichia coli in a medium of high osmolarity, which inhibits the expression of a gene coding for a protein called Omp F. See Mizumo, et al. "Regulation of Gene Expression by a Small RNA Transcript (micRNA) in Escherichia coli: K-12", Proc. Jap. Acad., 59, 335-338 (1983). The inhibition of OmpF protein production by the small mRNA transcript (mic-RNA, i.e. mRNA interfering complementary RNA) is likely due to the formation of a hybrid between the micRNA and the ompF mRNA over a region of approximately 80 bases including the Shine-Dalgarno sequence and the initiation codon.

A similar regulation by a small complementary mRNA has also been described for the Tn10 transposase gene, see Simons et al. "Translational Control of IS10 Transposition", Cell, 34, 683-691 (1983). In this case, however, the gene for the transposase Protein and the gene for the micRNA are transcribed in opposite directions off the same segment of DNA such that the 5'-ends of the transcripts can form a complementary hybrid. The hybrid is thought to inhibit translation of the transposase mRNA. However, the transposase situation is in contrast to the ompF situation in which the ompF gene and the micRNA gene (micF) are completely unlinked and map at 21 and 47 minutes, respectively, on the E. coli chromosomes.

It is an object of this invention to provide a technique useful for the regulation of gene expression of a cell and/or an organism.

It is another object of this invention to provide transformed cells and/or organisms having special properties with respect to the gene expression of the genetic material making up said organisms.

It is yet another object of this invention to provide DNA and viral or plasmid vectors containing the DNA, wherein said DNA is transcribed to produce mRNA which is complementary to and capable of binding or hybridizing to the mRNA produced by said gene to be regulated.

It is a further object of this invention to Provide an improved technique and materials useful in connection therewith for the regulation or inhibition of gene expression.

It is also an object of this invention to provide transformed organisms, having been transformed with plasmids or viral vectors containing a gene that produces a micRNA which regulates and/or inhibits the gene expression of a gene located within the host organism.

Another object of this invention is to provide DNA, or vectors including plasmids and viral vectors containing said DNA which is transcribed to produce an mRNA (micRNA) which is complementary to and capable of binding or hybridizing with the mRNA transcribed by the gene to be regulated.

How these and other objects of this invention are achieved will become apparent in the light of the accompanying disclosure and with reference to the accompanying drawings wherein:

FIGS. 1a, 1b, and 1c describe the construction of a subclone or a gene and various plasmids carrying the promoter region therefor;

FIG. 2 sets forth the nucleotide sequence of the promoter region and upstream region of an ompC gene of E. coli;

FIG. 4 illustrates the homologous sequences between the micF and the ompC genes of E. coli;

FIG. 7 illustrates the homology between the ompC mRNA and the lpp mRNA; and

SUMMARY OF THE INVENTION

Figure 2:
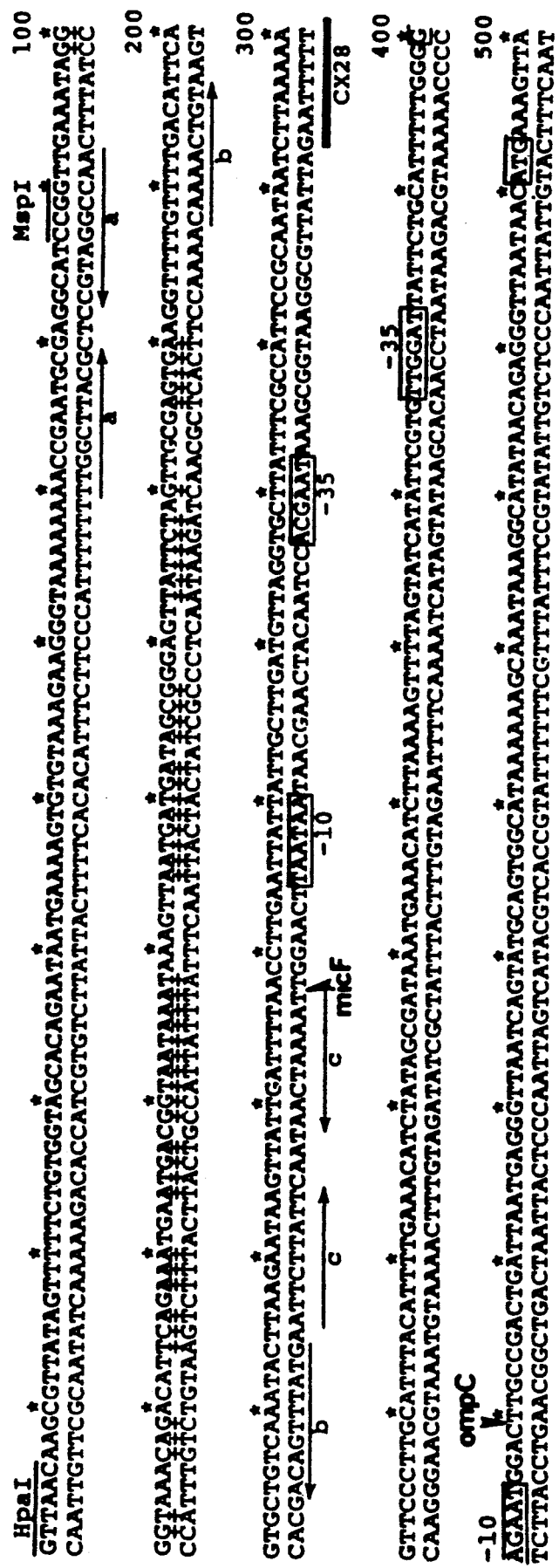

Gene expression in an organism in accordance with the practices of this invention is regulated, inhibited and/or controlled by incorporating in or along with the genetic material of the organism non-native DNA which transcribes to produce an RNA which is complementary to and capable of binding or hybridizing to a mRNA Produced by a gene located within said organism. Upon binding to or hybridization with the mRNA, the translation of the mRNA is prevented. Consequently, the protein coded for by the mRNA is not produced. In the instance where the mRNA translated product, e.g. protein, is vital to the growth of the organism or cellular material, the organism is so transformed or altered such that it becomes, at least, disabled.

In accordance with the practices of this invention there has been constructed a mic system designed to regulate the expression of a gene. More particularly, one can construct in accordance with the practices of this invention an artificial mic system to regulate the expression of any specific gene in E. coli.

Further, in accordance with the practices of this invention, a micRNA system for a gene is constructed by inserting a small DNA fragment from the gene, in the opposite orientation, after a promoter. Such a system provides a way, heretofore unknown, for specifically regulating the expression of any gene. More particularly, by inserting the micDNA fragments under the control of an inducible promoter, particularly as embodied in E. coli, the expression of essential E. coli genes can be regulated. It would appear, therefore, that in accordance with the practices of this invention, the inducible lethality thus-created may be an effective tool in the study of essential genes.

Hereinafter, in accordance with the practices of this invention, there is described the construction of an artificial mic system and the demonstration of its function utilizing several E. coli genes. The mic system in accordance with this invention is an effective way to regulate the expression of specific prokaryotic genes. This invention accordingly provides the basis for accomplishing similar regulation of biologically important genes in eukaryotes. For example, the mic system can be used to block the expression of harmful genes, such as oncogenes and viral genes, and to influence the expression substantially of any other gene, harmful or otherwise.

The practices of this invention are thus applicable to both procaryotic and eukaryotic cellular materials or microorganisms, including yeast, and are generally applicable to organisms which contain expressed genetic material.

Accordingly, in the practices of this invention from a genetic point of view as evidenced by gene expression, new organisms are readily produced. Further, the practices of this invention provide a powerful tool or technique for altering gene expression of organisms. The practices of this invention may cause the organisms to be disabled or incapable of functioning normally or may impart special properties thereto. The DNA employed in the practices of this invention can be incorporated into the treated or effected organisms by direct introduction into the nucleus of a eukaryotic organism or by way of a plasmid or suitable vector containing the special DNA of this invention in the case of a procaryotic organism.

DETAILED DESCRIPTION OF THE INVENTION

By way of further background of the practices of this invention, it has been found that gene expression of the major outer membrane proteins, OmpF and OmpC, of Escherichia coli are osmoregulated. The ompC locus was found to be transcribed bidirectionally under conditions of high osmolarity. The upstream stretch of mRNA of approximately 170 bases was found to inhibit the production of OmpF protein. This mRNA (micRNA) has a long sequence which is complementary to the 5'-end region of the ompF mRNA that includes the ribosome-binding site and the coding region of the first nine amino acid residues of pro-OmpF protein. Thus, it is proposed that the micRNA inhibits the translation of ompF mRNA by hybridizing with it. This novel mechanism can account for the observation that the total amount of the OmpF and of the OmpC proteins is always constant in E. coli.

The major outer membrane proteins of Escherichia coli, OmPF and OmpC, are essential proteins which function as passive diffusion pores for small, hydrophilic molecules. These matrix porin proteins are encoded by the structural genes ompF and ompC, which map at 21 and 47 min on the E. coli chromosome, respectively, see Reeves, P. in Bactrial Outer Membranes: Biogenesis and Function (ed. Inouye, M.) 255-291 (John Wiley and Sons, New York, 1979). The expression of these genes is regulated by the osmolarity of the culture medium. There is a strict compensatory production of both proteins: as the osmolarity of the culture medium increases, the production of OmpF protein decreases while the production of OmpC protein increases so that the total amount of the OmpF plus OmpC proteins is constant. This osmoregulation of the ompF and ompC genes is controlled by another unlinked locus, ompB, which maps at 74 min, see Hall, M. N. & Silhavy, T. J., J. Mol. Biol. 146, 23–43 (1981) and Hall, M. N. & Silhavy, T. J., J. Mol. Biol. 151, 1-15 (1981). The ompB locus contains two genes called ompR and envZ. The DNA sequences of both genes have been determined and their gene products have been characterized, see Wurtzel, E. T. et al., J. Biol. Chem. 257, 13685-13691 (1982) and Mizuno, T., et al., J. Biol. Chem, 257, 13692-13698 (1982). The EnvZ protein, assumed to be a membrane receptor protein, serves as an osmosensor transmitting the signal from the culture medium to the OmpR protein. The OmpR protein then serves as a positive regulator for the expression of the ompF and ompC genes. The ompF and ompC genes were sequenced, and extensive homology was found in their coding regions, however, there was very little homology in their promoter regions.

During the characterization of the ompC gene, the novel regulatory mechanism of gene expression mediated by a new species of RNA called mRNA interfering complementary RNA (micRNA) in accordance with this invention was discovered and/or elicited. MicRNA is produced from an independent transcriptional unit (the micF gene). This gene is located immediately upstream of the ompC gene but is transcribed in the opposite direction. The 174-base micRNA blocks the translation of the ompF mRNA by hybridizing to it. Since the production of micRNA is assumed to be proportional to the production of ompC mRNA, this regulatory mechanism appears to be a very efficient way to maintain a constant total amount of OmpF and OmpC proteins.

A DNA Fragment Suppressing ompF Expression

While characterizing the ompC promoter, it was found that a DNA fragment of approximately 300 bp, located upstream of the ompC promoter, completely blocked the production of OmpF protein when OmPF+ cells were transformed with a multi-copy plasmid harboring this DNA fragment. For this experiment, plasmid pMY150 was constructed from the original ompC clone, pMY111, see Mizuno, T. et al., *J. Biol. Chem.* 258, 6932-6940 (1982), by changing the HpaI sites of pMY111 to XbaI sites followed by removal of the 1.1 kb SalI fragment as described in FIG. 1a of FIG. 1.

FIG. 1 shows the construction of the subclone of the ompC gene and various plasmids carrying the ompC promoter region.

(a) Schematic presentation of the subcloning of the ompC gene. Plasmid pMY111 carrying a 2.7 Kb *E. coli* chromosomal DNA in pBR322 was described previously. The plasmid (1 ug of DNA) was digested with HpaI and religated in the presence of an XbaI linker (CTCTAGAG, 150 p mole). Thus, a 400 bp HapI fragment was removed and a unique XbaI site was newly created (pMY100). Plasmid pMY100 (1 μg of DNA) was further digested with SalI and religated to remove a 1 1 kb SalI fragment (pMY150). In order to obtain an ompC promoter fragment of different sizes, plasmid pMY150 was digested by Bal31 nuclease after cleavage of the unique BglII site (see FIG 1b). Subsequently, the plasmid was religated in the presence of an XbaI linker. Plasmid pCX28, thus constructed, is one of clones carrying approximately a 300-bp XbaI-XbaI fragment as shown in FIG. 1b.

(b) Simplified restriction map of the Plasmid pMY150 carrying the entire ompC gene. The 1.8 Kb HindIII-SalI fragment (boxed region) in pBR322 contains the entire ompC coding region as well as the 5'- and 3'-noncoding region. Transcription of the ompC gene proceeds in the direction shown by an arrow. A bidirectional arrow indicates an approximate deleted region (ca. 600 bp) for plasmid pCX28.

(c) Various β-galactosidase (lacZ) gene fusions to the DNA fragments derived from the ampC promoter and its upstream region: Plasmid I, 507-bp XbaI-RsaI fragment was isolated from pMY150 (an RsaI site is present just downstream of the ATG codon), and inserted between XbaI-SmaI sites of plasmid pICIII which is derived from plasmid pINIII carrying the lacz gene. During the ligation, a HindIII linker was inserted between the RsaI and SmaI ligation site. The XbaI-HindIII fragment was isolated from the plasmid thus constructed and reinserted into plasmid pKM005 to create a lacZ gene fusion in the right reading frame. Characteristic features of plasmids pICIII and pKM005 were described previously. Plasmids II and IV carrying approximately 430-bp MspI-BamHI fragment was isolated from clone I (a BamHI site is present just downstream of the ATG codon for the β-galactosidase coding sequence in plasmid I), and treated with S1 nuclease to create blunt ends. After adding XbaI linkers at both ends, the XbaI-XbaI fragment thus obtained was inserted into plasmid pKM005 at its XbaI site in the possible two orientations. Plasmids III and v, an approximately 300 bp XbaI-XbaI fragment was isolated from plasmid pCX28 (FIG. 1a) and inserted into plasmid PKM005 at its XbaI site in the two possible orientations. These plasmids (I-V) were transformed into a lacZ deletion strain SB4288 (F⁻ recA thi-1 relA ma124 spc12 supE-50 proB lac), and those β-galactosidase activities were tested on MacConkey plates (Difco). Results are shown as LacZ+ or LacZ−. Ability of these clones to inhibit the expression of OmpF protein are also shown as MicF+ or MicF−.

The resulting plasmid, pMY150 (FIG. 1b) contains the entire coding region of the ompC gene and approximately 500 bp of upstream sequences including the ompC promoter and the DNA encoding the 5'-end untranslated region of ompC mRNA. In order to obtain an ompC promoter fragment of different sizes, pMY150 was digested by Bal31 nuclease at the unique BglII site, followed by the addition of XbaI linkers. The plasmid constructed in this manner carry XbaI fragments that vary in size due to the position of the XbaI site furthest from the SalI site (see FIG. 1b). The different XbaI fragments were subsequently transferred to a promoter-cloning vector, pKM005 which can express the lacZ gene only when a promoter fragment is inserted in the right orientation into its unique XbaI site. These experiments revealed that transcription of the ompC gene initiates at a site located between 390 and 440 bp downstream from the upstream XbaI site (originally HpaI site). Surprisingly, *E. coli* transformed with these pKM005 derivatives, including the clone of the shortest XbaI fragment of only 300 bp, CX28 (subcloned from pCX28; FIG. 1a and b) lost the ability to produce OmpF protein. OmpF protein was clearly produced in the host cells (ompB+ ompF+ ompC+), while the same cells carrying the clone of the CX28 fragment were not able to Produce OmPF protein. The same effect could be observed with cells harboring a clone of a longer fragment such as plasmid I in FIG. 1c. In this clone the lacZ gene was fused immediately after the initiation codon of the ompC gene resulting in the LacZ+ phenotype of the cells carrying this plasmid. However, when the XbaI-MspI fragment of 87 bP was removed from plasmid I, the cells carrying the resulting plasmid (plasmid II in FIG. 1c) were able to produce OmpF protein. It should be mentioned that a similar DNA fragment of 430 bP in length containing the upstream region of the ompF gene did not block the production of both OmpF and OmpC proteins.

DNA Sequence Homology Between CX28 and the ompF Gene

The results described above demonstrate that the stretch of DNA approximately 300 bp long, located upstream of the ompC promoter, is able to block ompF expression. In order to elucidate the function of this DNA fragment (CX28), the DNA sequence of this region was determined.

Reference is now made to FIG. 2 which shows the nucleotide sequence of the promoter region and upstream of the ompC gene. Restriction DNA fragments prepared from pMY111 or PMY150 were labeled at their 3'-end by the method of Sakano et al., Nature. 280, 288-294 (1979), using [$\alpha$-$^{32}$P] dNTP's and DNA polymerase I large fragment (Klenow fragment). Singly end-labeled DNA fragment was obtained by digestion with a second restriction enzyme. DNA sequence were determined by the method of Maxam and Gilbert, *Methods in Enzymology* 65, 499-560 (1981), using 20%, 10% and 6% polyacrylamide gels in 7M urea. The RNA polymerase recognition site (−35 region) and the Pribnow box (−10 region) for the ompC and micF promoter, as well as the initiation codon of the ompC gene are boxed. The transcriptional initiation sites are determined by S1 nuclease mapping for the ompC and micF genes.

FIG. 2 shows the DNA sequence of 500 bP from the XbaI site (originally HpaI) to the initiation codon, ATG, of the ompC gene. The DNA sequence downstream of residue 88 was determined Previously. It was found that the sequence from residue 99 to 180 (FIG. 2) has 70% homology with the 5'-end region of the ompF mRNA which includes the Shine-Dalgarno sequence, the initiation codon, and the codons for the first nine amino acid residues of pro-OmpF protein (bases marked by + are homologous to the ompF sequence). A plausible model to explain the above result is that the 300-bp CX28 fragment (FIG. 1c) contains a transcription unit which is directed towards the region upstream of the ompC gene so that the RNA transcript from this region has a sequence complementary to the ompF mRNA. The hybridization between the two RNAs thus blocks the translation of ompF mRNA to OmpF protein.

Existence of a New Transcription Unit

To determine whether the CX28 fragment contained an independent transcription unit oriented in a direction opposite from the ompC gene, the lacZ gene was fused at two different sites within the CX28 fragment. In plasmid V, the CX28 fragment was inserted in the opposite orientation with respect to plasmid III (FIG. 1c). This clone was still fully active in suppressing the Production of OmpF protein, although it did not produce β-galactosidase (LacZ−) (see FIG. 1c). When the fusion junction was shifted to the MspI site at nucleotide 88 (FIG. 2, also see FIG. 1c), the newly constructed clone (plasmid IV) was capable of producing β-galactosidase. However, this plasmid was no longer able to suppress the production of OmPF protein. Although this plasmid contains additional DNA (approximately 200 bp) upstream from the lacZ and the CX28 sequences (from residue 300 to 500; FIG. 2), this should not affect the functions of the CX28 fragment since plasmid V is fully active in the suppression of OmpF protein production. These results demonstrate that there is a transcription unit in the CX28 fragment which is independent from the ompC gene promoter and that the CX28 fragment and the ompC gene are transcribed in divergent directions. The fact that plasmid IV can produce β-galactosidas and plasmid IV do not, indicates that the CX28 transcription unit terminates between residue 1 and 88 (FIG. 1c). In fact, a very stable stem-and-loop structure can form between nucleotides 70 and 9 (arrows with letter a in FIG. 2) which is followed by oligo-[T]. This structure is characteristic of ρ-factor independent transcription termination sites in prokaryotes. The ΔG value for this structure was calculated to be −12.5 Kcal according to Salser. W., *Cold Spring Harbor Symp. Quant. Biol.* 12, 985-1002 (1977).

The initiation site for the CX28 transcript was positioned at nucleotide 237 (FIG. 2) by S1-nuclease mapping. This result indicates that the CX28 DNA fragment is transcribed to Produce a transcript of 174 nucleotides. This was further proven by Northern blot hybridization. In the RNA preparation extracted from cells carrying plasmid III (FIG. 1c), an RNA species is clearly observed to hybridize with the CX28 fragment, which migrates a little slower than 5S RNA. In the control cells, only a small amount of the same RNA was detected. The size of the RNA (CX28 RNA) was estimated on gel to be approximately 6S which is in very strong agreement with the size estimated from the sequence (174 bases).

Function of the CX28 RNA

Figure 3:
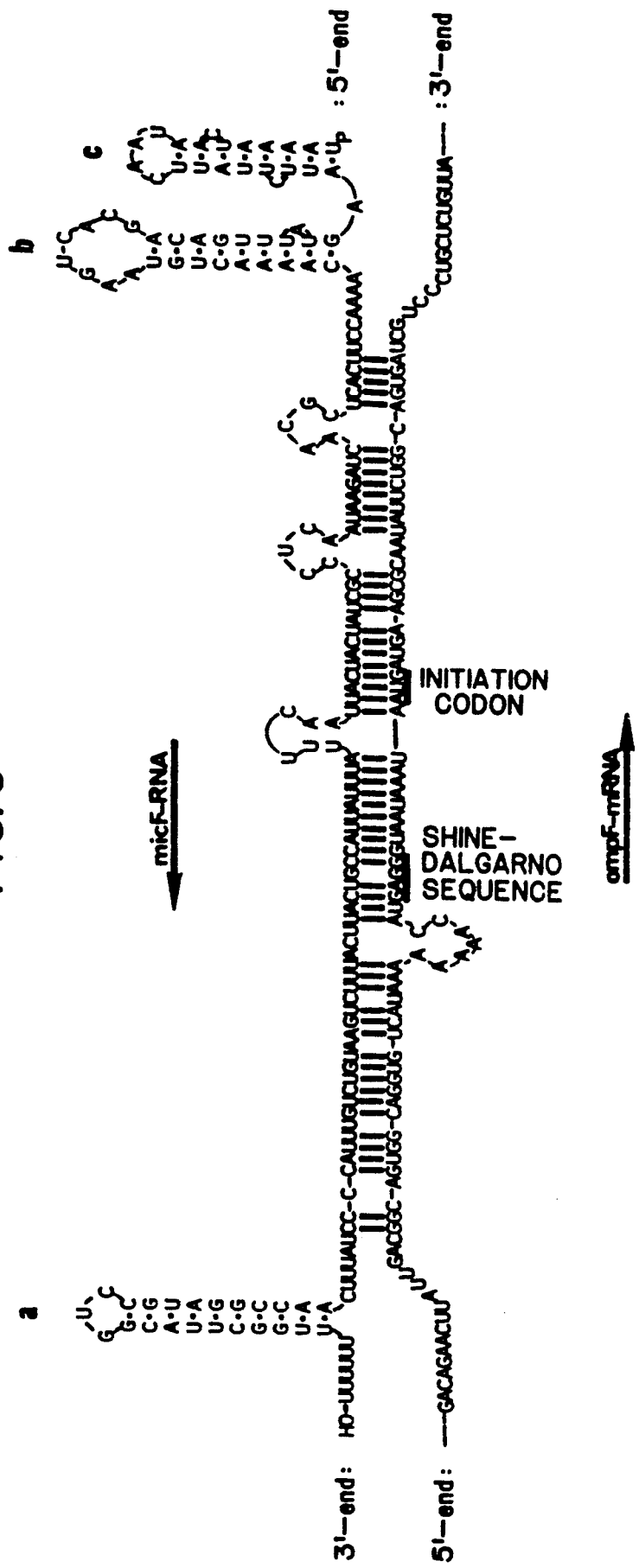
FIG. 3 illustrates the hybrid formation between certain RNA in accordance with the practices of this invention.

As pointed out earlier, the CX28 DNA fragment has extensive homologies with a portion of the ompF gene. Thus, part of CX28 RNA is complementary to the ompF mRNA and can form an extremely stable hybrid with the ompF mRNA as shown in FIG. 3. The ΔG value for this hybrid formation was calculated to be −55.5 Kcal Forty-four bases of the 5'-end untranslated region of ompF mRNA, including the Shine-Delgarno sequence for ribosome-binding and 28 bases from the coding region, are involved in the hybrid formation. This hybrid structure is sandwiched by the two stable stem-and-loop structures of the CX28 RNA; one for the 3'-end ρ-independent transcription termination signal (loop a) and the other at the 5'-end (loop b). The ΔG values for loops a and b were calculated to be −12.5 and −4.5 Kcal, respectively.

Referring now to FIG. 3 of the drawings, there is illustrated therein hybrid formation between micF and ompF mRNA. The sequence of micF RNA corresponds to the sequence from residue 237 to 64 in FIG. 2. The ompF mRNA sequence was cited from Inokuchi, K. et al., *Nucleic Acids Res.* 10, 6957-6968 (1982). The ΔG values for the secondary structures a b and c were calculated to be −12.5, −4.5 and +2.9 Kcal, respectively.

In FIG. 3 another loop (loop c) is shown. This loop, however, is unlikely to be formed because of its ΔG value (+2.9 Kcal). It appears that the formation of the hybrid blocks the translation of ompF mRNA. This would explain why clones carrying the CX28 DNA fragment suppress the production of OmpF protein Thus, CX28 RNA is designated as the mRNA-interfering complementary RNA for ompF (micRNA for ompF) and the gene is designated micF. It should be noted that when loop a was eliminated by fusing the micF gene with the lacZ gene, the MicF function was abolished (plasmid IV, FIG. 1c). This may be due to the stability of the micF RNA or alternatively due to the requirement of loop a for the micF function.

It seemed of interest to examine whether the micF gene is under the control of the ompB locus as is the ompC gene. Various lacZ clones were therefore put into four different ompB mutants. Reference is now made to Table I.

TABLE I

β-Galactosidase Activities of Various Promoter-lazZ Gene Fusion Clones in ompB Mutant Strains

| Plasmids Strains | β-Galactosidase Activity (U) | | | |
|---|---|---|---|---|
| | pKM004 (lpp$^p$-lacZ) | Plasmid I (ompC$^p$-lacZ) | Plasmid IV (micF$^p$-lacZ) | pOmpF$^p$-Al (ompF$^p$-lacZ) |
| Mc4100 (wild type) OmpC+ OmpF+ | 1360 | 1808 | 796 | 2071 |
| MH1160 (ompR1) OmpC− OmpF− | 1415 | 102 | 133 | 43 |
| MH760 (ompR2) OmpC− OmpF+ | 1219 | 21 | 102 | 1521 |
| MH1461 (envZ) OmpC+ OmpF− | 905 | 1500 | 616 | 1063 |

Various ompB mutant strains, MC4100 (F−lacV169 araD139 rspL thiA tibB relA; wild type), MH1160 [ompB101 (ampR1) mutant from MC4100] MH760 [ampB427 (ompR2) mutant from MC4100], MH1461 [tpoII (envZ) mutant from MC4100] were transformed by various promoter-lacZ gene fusion clones Cells were grown in 10 ml of nutrient broth at 37° C. to Klett unit of 1.2. 100 ul of the cultures were used for β-galactosidase activity measurement according to the method of Miller, H. J., in *Experiments of Molecular Genetics* (ed. Miller, H. J.) 352-355 (Cold Spring Harbor Laboratory, New York (1972)). Plasmid pK004 was derived from pKM005 and pKM004 contains the lpp (the gene for outer membrane lipoprotein) promoter fused to the lacZ gene. Plasmid I and IV are described in FIG. 1c. Plasmid pOmpF$^p$-Al contains the lacZ gene under the control of the ompF promoter.

As shown in Table I, the lacZ gene under micF control (plasmid IV in FIG. 1C) produces β-galactosidase in the same manner as the lacZ gene under ompC promoter control (plasmid I in FIG. 1C) high β-galactosidase activity was found in both the wild type and envZ− strains but low activity was observed in ompR1− and ompR2− mutants. On the other hand, the lacZ gene under the control of the ompF promoter was not expressed in the omPR1− cells. In addition, lacZ gene under the control of the lipoprotein promoter, used as a control, was expressed in all strains. These results indicate that the micF gene is regulated by the ompB locus in the same fashion as the ompC gene. It is interesting to note that the lacZ gene under the control of the ompF promoter is constitutively expressed in the envZ− (Ompc+ GmpF−) strain. This suggests that the OmpF− phenotype of this envZ− strain is due to the inhibition of translation of the ompF mRNA by micRNA.

Promoters of the micF and ompC Genes

Since both the micF and ompC genes appear to be regulated by the ompB locus, the promoters of these genes should have sequence homologies. In order to search for the homologies, the transcription initiation site for the ompC gene was first determined by S1-nuclease mapping. Major transcription initiation takes place at the T residues at position 410 and 411 (FIG. 2; also see FIG. 4).

Figure 4:
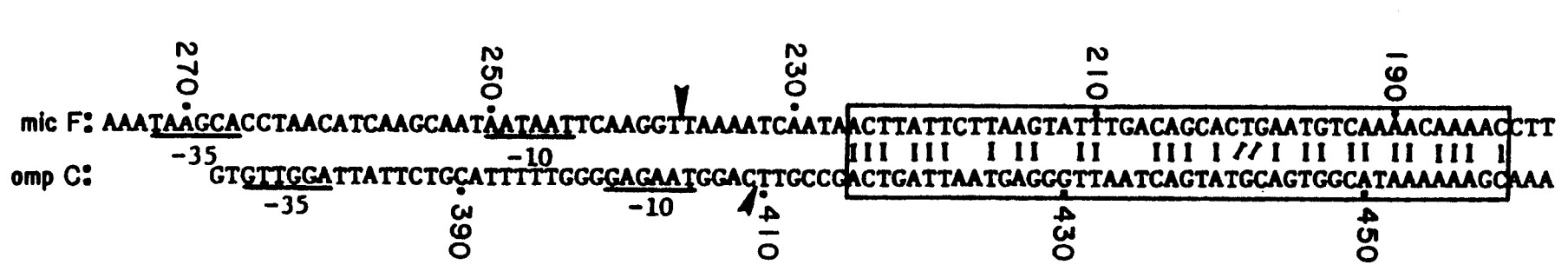

In FIG. 4 the homologous sequences between the micF and the ompC genes are shown. Nucleotide numbers correspond to those in FIG. 2. The sequences in the box show the homologous sequences between the two genes. Bars between the two sequences indicate the identical bases. The arrows indicate the transcription initiation sites. The −10 and −35 regions are underlined.

Thus, −10 regions for the micF and ompC genes are assigned as AATAAT (nucleotides 250 to 245 in FIG. 2) and GAGAAT (nucleotides 400 to 405 in FIG. 2), respectively (FIG. 4), both of which show good homology to the consensus sequence, TATAAT. RNA Polymerase recognition sites, (−35 regions), for the micF and ompC genes are also assigned as TAAGCA and TTGGAT, respectively (FIG. 4), both of which show 50% homology to the consensus sequence, TTGACA. However, no significant sequence homologies are found between the micF promoter of 63 bp (nucleotides 300 to 238) and the ompC promoter (nucleotides 301 to 409 in FIG. 2). On the other hand, homologous sequences are found in the 5'-end regions of both the transcripts as shown in FIG. 4. Twenty-eight out of 44 bases are homologous (64% homology), and these regions are Probably the sites recognized by OmpR protein It is interesting to note that a homologous sequence to these sequences has also been found in the 5'-end untranslated region of ompF mRNA. Binding experiments of the micF gene and the ompC gene with purified OmpR protein are now in progress.

As indicated hereinabove, regulation of gene expression in *E. coli* is generally controlled at the level of transcription. It has been well established that expression of some genes are suppressed by their specific repressors or activated by their specific inducers. Positive protein factors such as cAMP receptor protein and OmpR protein are also known to regulate gene expression at the level of transcription. Another transcriptional regulatory mechanism is attenuation which plays an important role in controlling expression of operations involved in the biosynthesis of various amino acids of other compounds, see Kolter, R. & Yanofsky, C. *Ann. Rev. Genet* 16, 113-134 (1982).

In addition, some proteins have been shown to regulate gene expression at the level of translation. The results herein demonstrate the regulation of bacterial gene expression at the level of translation by means of a complementary RNA factor to the translational start region. This novel regulatory mechanism mediated by micRNA is illustrated in FIG. 5.

Figure 5:
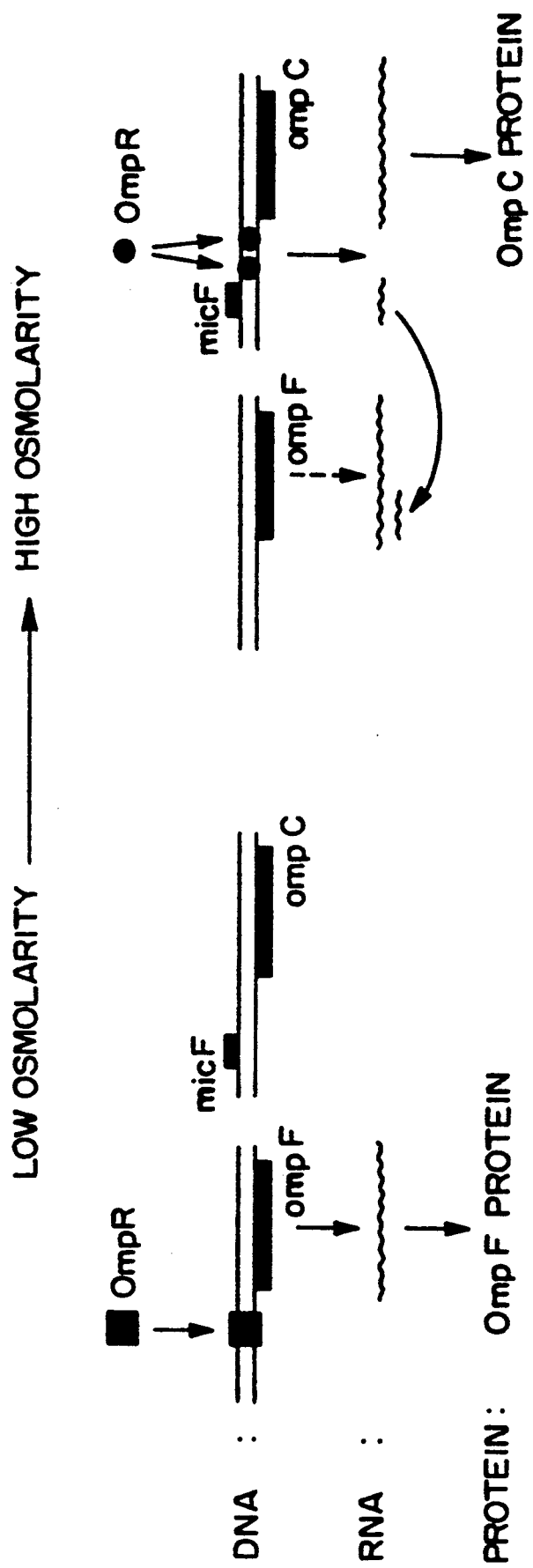
FIG. 5 illustrates a possible model for the role of micF RNA useful in and in accordance with the practices of this invention.

FIG. 5 illustrates a possible model for the role of micF RNA. OmPR protein binds to the ompF gene under the low osmolarity and promotes the production of OmpF protein. Under the high osmolarity, OmpR protein binds to both the micF and the ompC genes. The micF RNA thus produced hybridizes with the ompF mRNA to arrest its translation.

The possibility that micRNA blocks the expression of the ompF gene at the level of transcription has not been ruled out. However, this is highly unlikely since the lacZ gene fused with the ompF promoter was expressed in the envZ− cells (OmPC+ OmpF−; Table 1. In this case lacZ expression is probably due to the inability of lacZ mRNA transcribed from the clone to form a stable hybrid with micRNA. Furthermore, if micRNA is able to bind the nonsense strand of the ompF gene, it would more likely stimulate gene expression rather than block it, since the binding would make the ompF gene more accessible to RNA polymerase.

Regulation by micRNA appears to be an extremely efficient way to block production of a specific protein without hampering other protein production. At present, the relative ratio between micRNA and ompC production is not known ($\beta$-galactosidase activities in Table I do not necessarily reflect their accurate promoter activities, since the promoter regions were not inserted in the same fashion, see FIG. 1c). However, it is reasonable to assume that the micRNA and the ompC are produced coordinately. Therefore, when OmpC protein is produced, micRNA is produced in the same manner. micRNA then blocks the production of OmpF protein proportionally, so that the total amount of OmpC plus OmpF protein is constant.

The binding of micRNA to the ribosome-binding site and the initiation codon is a very effective way to block the translation of the particular mRNA. A similar mechanism has been proposed to explain a translational block in a mutant of bacteriophage T7. It was suggested that the sequence of the 3'-end of a mutant mRNA hybridizes with its own ribosome-binding site to block translation, see Saito, H. & Richardson, C. C., *Cell*, 27, 533–542 (1981). It seems reasonable that the micRNA regulatory system may be a general regulatory phenomenon in *E. coli* and in other organisms including eukaryotes. It is a particularly attractive and rapid mechanism to very rapidly stop the formation of a protein or to control the ratio of one protein with another. RNA species may have additional roles in the regulation of various cellular activities. In fact, small RNA species have been shown to be involved in the regulation of DNA replication of some plasmids.

Construction of an Artificial Mic Gene

The micF gene produces a 174-base RNA that blocks production of the OmpF protein. This small RNA has two stem-and-loop structures, one at the 3.-end and the other at the 5'-end. Since these structures are considered to play an important role for the function of the micRNA, it was attempted to use these features in the construction of an artificial mic system using the gene for the major outer membrane lipoprotein (lpp) cloned in an inducible expression vector, pIN-II, see Nakamura et al., "Construction of Versatile Expression Cloning Vehicles Using the Lipoprotein Gene of *Escherichia coli*", *EMBO J.*, 1, 771–775 (1982).

Figures 6A, 6B:
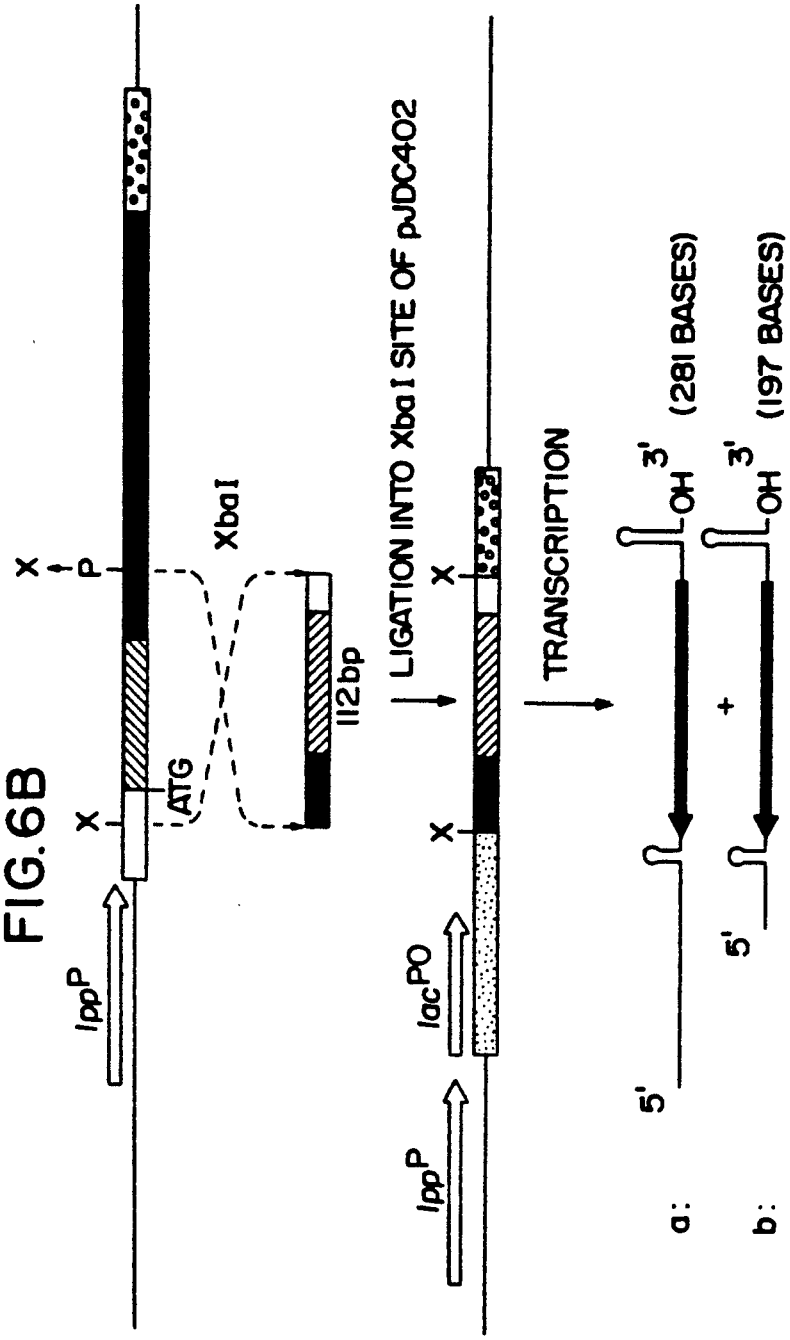
FIGS. 6a and 6b illustrate the construction of mic vector pJDC402 and mic(lpp)

PIN-II vectors are high expression vectors that have the lac$^{po}$ downstream of the lipoprotein promoter, thus allowing high level inducible expression of an inserted gene. The pIN-II promoter was fused to the lpp gene at a unique XbaI site immediately upstream of the Shine-Dalgarno sequence of the lpp mRNA. The resulting plasmid was designated as pYM140. When the expression of the lpp gene, in pYM140, is induced by isopropyl-$\beta$-D-thiogalactoside (IPTG), a lac inducer, the RNA transcript derived from the lpp gene has a possible stem-and-loop structure (at the 5' end). Immediately upstream of the unique XbaI site, see FIG. 6-A, is another stable stem-and-loop structure at its 3' end. The latter loop is derived from the $p$-independent transcription termination signal of the lpp gene. The construction of a general mic cloning vector. pJDC402 was achieved by removing the DNA fragment in pMH044 between the two loops as shown in FIG. 6-A. An RsaI site immediately upstream of the termination site was changed to an EcoRI site by partial digestion of pYM140 followed by insertion of an EcoRI linker. The resulting plasmid, pMH044 was partially digested with EcoRI, followed by a complete digestion with XbaI. The single stranded portions of the linear DNA fragment were filled in with DNA polymerase I (large fragment), and then treated with T4 DNA ligase, resulting in the formation of the plasmid, pJDC402, which lost the fragment between the XbaI and the RsaI sites.

As a result of this procedure, both an EcoRI and an XbaI site were recreated at the junction. Thus the unique XBaI site can serve as the insertion site for any DNA fragment, and the RNA transcript from the artificial mic gene produces an RNA which has a similar structure to the micF RNA; the portion derived from the inserted DNA is sandwiched by two loop structures, one at the 5' and one at the 3'-end.

The following is a more detailed description of FIG. 6-A and FIG. 6-B. As illustrated in FIG. 6-A for the construction of PJDC402, restriction sites are indicated as follows: X, XbaI; P, PvuII; E, EcoRI. lpp$^p$ and lac$^{po}$ are the lipoprotein promoter and the lactose promoter operator, respectively. Amp$^r$ is the Ampicillin resistance gene. Cross hatches represent the lipoprotein promoter. Solid dots represent the lactose promoter operator. Slashes indicate the lipoprotein signal sequence, and the solid bar represents the coding region for the mature portion of the lipoprotein. The open dots represent the transcription termination region derived from the lpp gene. The open bar represents the 5' nontranslated region of the lipoprotein mRNA.

Figure 8:
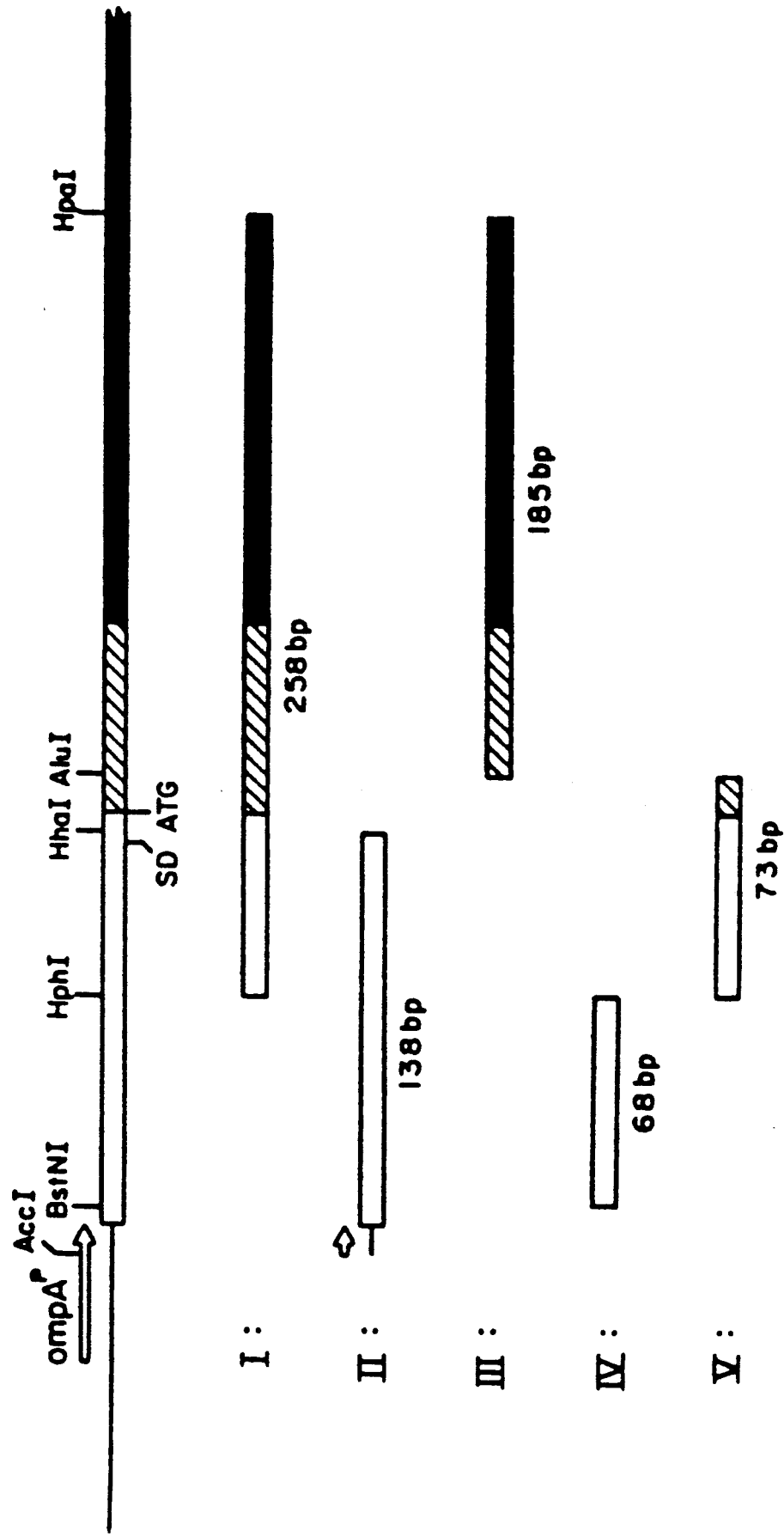
FIG. 8 illustrates fragments used to construct mic-(ompA) genes.

In FIG. 6-8 for the construction of mic (lpp) pJDC412, open arrows represent promoters. The PvuII site was converted to an XbaI site by inserting an XbaI linker (TCTAGAG). This fragment was inserted into the unique XbaI site of pJDC402 in the reverse orientation forming pJDC412. a and b show the mic(lpp) RNAs initiating at the lpp and lac promoters, respectively.

Construction of the mic(lpp) Gene

Using the mic cloning vector PJDC402, it was first attempted to create a mic system for the lpp gene of *E. coli*, in order to block the synthesis of the lipoprotein upon induction of the mic(lpp) gene. For this purpose it is necessary to first isolate the DNA fragment containing the Shine-Dalgarno sequence for ribosome binding, and the coding region for the first few amino acid residues of prolipoprotein. To do this the PvuII site immediately after the coding region of prolipoprotein signal peptide was changed to an XbaI site by inserting an XbaI linker at this position. The resulting plasmid was then digested with XbaI, and the 112-bp XbaI-XbaI (originally PvuII-XbaI) fragment was purified. This fragment encompassing the Shine-Dalgarno sequence and the coding region for the first 29 amino residues from the amino terminus of prolipoprotein was purified. This fragment was then inserted into the unique XbaI site of PJDC402 in the opposite orientation from the normal lpp gene. The resulting plasmid, designated as pJDC412, is able to produce mic(lpp) RNA, an RNA transcript complementary to the lpp mRNA, upon induction with IPTG.

The inclusion of a HinfI site immediately upstream of the lpp promoter and another one immediately downstream of the transcription termination site in the mic expression vector PJDC402 is important. These two HinfI sites can be used to remove a DNA fragment Containing the entire mic transcription unit which can then be inserted back into the unique ovuII site of the vector. In this manner, the entire mic gene can be duplicated in a single plasmid. One would expect a plasmid containing two identical mic genes to produce twice as much micRNA as a plasmid containing a single mic gene. Such a plasmid was constructed containing two mic(lpp) genes and designated as PJDC422.

Expression of the mic(lpp) Gene

In order to examine the effect of the artificial mic(lpp) RNA, cells were pulse-labeled for one minute, with [$^{35}$S]-methionine, one hour after induction of the mic(lpp) with 2mM IPTG. The cells harboring the vector, pJDC402, produce the same amount of lipoprotein either in the absence or the presence of the inducer, IPTG, as quantitated by densitometric scanning of the autoradiogram and normalizing. Lipoprotein production was reduced approximately two-fold in the case of cells carrying pJDC412 in the absence of IPTG and approximately 16-fold in the presence of IPTG. The reduction in lipoprotein synthesis in the absence of IPTG is attributed to incomplete repression of the mic(lpp) gene. In the case of cells carrying pJDC422, where the mic(lpp) gene was duplicated, lipoprotein production is now reduced 4-fold in the absence of IPTG, and 31-fold in the presence of IPTG. These results clearly demonstrate that the production of the artificial mic(lpp) RNA inhibits lipoprotein production, and that the inhibition is proportional to the amount of the mic(lpp) RNA produced It should be noticed that the mic(lpp) RNA is specifically blocking the production of lipoprotein, and that it does not block the production of any other proteins except for OmPC Protein. The fact that the induction of the mic(lpp) gene reduces the production of the OmpC plus OmpF proteins was found to be due to unusual homology between the lpp and the ompC gene as discussed hereinafter.

There are several mechanisms by which the mic inhibition may occur. One mechanism is that the micRNA binds to the mRNA preventing the ribosome from binding the mRNA. Other possible mechanisms include: destabilization of the mRNA, attenuation of the mRNA due to premature termination of transcription, or inhibition of transcription initiation. If the inhibitory effect of the micRNA is solely at the level of attenuation or transcription initiation one would expect the mic effect to be somewhat delayed due to the fact that the functional half-life of the lipoprotein mRNA is 12 minutes. Therefore, it was examined how rapidly lipoprotein production is inhibited upon induction of the mic(lpp) RNA by pulse-labeling E. coli JA221/F'lacI$^q$ harboring pJDC412, with [$^{35}$S]-methionine at various time points after induction with IPTG. It was determined that lipoprotein production was maximally inhibited by 16-fold within 5 minutes after the addition of IPTG. This result indicates that inhibition of lipoprotein production is primarily due to the binding of the mic(lpp) RNA to the lpp mRNA, resulting in the inhibition of translation of the lpp mRNA and/or destabilization of the mRNA.

lpp mRNA Production in the Presence of mic(lpp) RNA

It appeared interesting to examine whether the mic(lpp) RNA also affects the level of the lpp mRNA, since the expression of the micF gene substantially reduced the amount of the ompF mRNA. For this purpose, total cellular RNA one hour after the induction of the mic(lpp) gene with IPTG was isolated. The RNA preparation was analyzed after electrophoresis in a formaldehyde agarose gel and subsequently transferred onto nitrocellulose paper. The Paper was then hybridized with a probe specific to the mic(lpp) RNA, or to the lpp mRNA. A probe specific for the ompA mRNA was used as an internal control. Again PJDC402 shows no difference in the production of the lpp mRNA in the absence or presence of IPTG. Due to the fact that the double stranded primer used to make the probe for these experiments contains a portion of the lac operon, the probes hybridize to any transcript containing the lac promoter such as the mic(lpp) RNA from JDC412 and the short nonsense transcript from pJDC402.

Cells harboring pJDC412 contain a reduced amount of the lpp mRNA in the absence of IPTG and a greatly reduced amount of the lpp mRNA in the presence of IPTG. The production of the mic(lpp) RNA in the absence and the presence of IPTG in cells harboring pJDC412 was shown. Therefore, even in the absence of IPTG, a significant amount of the mic(lpp) RNA is produced. This is consistent with the results of the lipoprotein production observed earlier. The fact that the lpp mRNA disappears upon induction of the mic(lpp) RNA indicates that the mechanism of action of the micRNA is not solely at the level of translation. Tests demonstrated there are two mic(lpp) RNAs of different sizes. The sizes of these transcripts were estimated to be 281 and 197 bases, which correspond to transcripts initiating at the lipoprotein promoter (the larger RNA) and initiating at the lac promoter (the smaller RNA).

Inhibition of OmpC Production with the mic(ompC) Gene

An almost complete inhibition of OmpC synthesis by artificially constructing mic(ompC) genes was achieved. The first construct, pAM320, carrying two mic(ompC) genes gives rise to an RNA molecule complementary to 20 nucleotides of the leader region and 100 nucleotides of the coding region of the ompC mRNA. This was done by changing the unique BglII site in the ompC structural gene and the MnlI site, 20 nucleotides upstream of the ATG initiation codon to XbaI sites. The resulting 128-bp XbaI fragment was then inserted into pJDC402 in the opposite orientation from the OmpC gene and a second copy of the mic-(ompC) gene was introduced in a manner similar to that described for the pJDC422 construction. The resulting plasmid, pAM320, has the second mic(ompC) gene inserted in the orientation opposite to the first one. Reversing the orientation of the second mic gene did not change the expression or stability of the plasmid. A second construct, pAM321, was designed to extend the complementarity between the micRNA and the ompC mRNA to include a longer leader sequence than in the case of pAM320, 72 nucleotides of the leader region instead of 20. This plasmid was constructed as described for PAM320, except that the MnlI site changed to an XbaI site was located 72 nucleotides bp upstream of the ompC initiation codon.

Commassie Brilliant Blue stained gel patterns of the outer membrane proteins isolated from E. coli JA221/F'lacI$^q$ harboring the mic cloning vector pJDC402, PAM320 and pAM321 were obtained. The effect of the addition of IPTG was clearly seen by the appearance of β-galactosidase. The induction of the mic(ompC) RNA from pAM320 caused a substantial decrease (approximately 5-fold) in OmpC Production, compared to PJDC402. Induction of the longer mic-(ompC) RNA from pAM321 decreased OmpC synthesis more dramatically (approximately 20-fold compared to pJDC402).

OmpC production could hardly be detected in the cells harboring PAM321 when they were pulse-labeled for one minute after a one-hour induction with IPTG. In the same experiment, OmpC synthesis decreased approximately 7-fold when the mic(ompC) gene in cells harboring pAM320 was induced with IPTG. Marked decreases in OmpC expression were also observed when plasmids containing single copies of the mic-(ompC) genes were induced. Again, the longer mic-(ompC) gene had a greater effect. The increased efficiency of mic-mediated inhibition with pAM320 may indicate that the effectiveness of the micRNA function is related to the extent of complementarity to the 5'-end of the mRNA.

It was interesting to note that the synthesis of either of the mic(ompC) RNAs described above caused a decrease not only in OmPC synthesis but also in lipoprotein synthesis. This inhibitory effect of the mic-(ompC) RNA on lipoprotein production appears to be due to the unexpected homology between the lpp mRNA sequence and the ompC mRNA as illustrated in FIG. 2. This feature explains why pAM320 and pAM321 are exerting a mic effect on lipoprotein production. Such an explanation would predict that induction of the mic(lpp) RNA from pJDC412 and PJDC422 should decrease the synthesis of the OmpC protein, and this was found to be the case.

In FIG. 7, a region of homology between the lpp mRNA (top line) and the ompC mRNA (bottom line) is illustrated. Bars connect identical bases. Both mic-(ompC) RNAs have the potential to hybridize across this homologous region. The Shine-Dalgarno Sequences (S.D.) and AUG initiation codons are boxed.

Inhibition of OmpA Production with mic(ompA) RNA

In an effort to determine what components contribute to the effectiveness of a micRNA, several mic genes were constructed from the ompA gene. The ompA gene was selected for this because the leader and the coding regions of the ompA mRNA have been characterized extensively. Five DNA fragments (see I through V of FIG. 8) were individually cloned into the XbaI site of pJDC402 in the orientation promoting the production of mic(ompA) RNAs. The resulting mic(ompA) plasmids containing fragments I-V were designated as pAM301, pAM307, pAM313, pAM314, and pAM318, respectively. Each plasmid contains only one copy of the described mic(ompA) gene.

In FIG. 8, the top line shows the structure of the *E. coli* ompA gene The arrow represents the promoter and the open bar represents the region encoding the 5'-leader region of the ompA mRNA. The slashed bar and shaded bar represent the portions of the ompA gene encoding the signal sequence and the mature OmPA protein, respectively. Restriction fragment I (HphI-HpaI) was inserted into the XbaI site of pJDC402, see FIG. 6-A, in the orientation opposite from that depicted here, as outlined in FIG. 6-B for mic(lpp), to create the plasmid, pAM301. The other mic(ompA) plasmids were similarly constructed from: fragment II, pAM307; fragment III, pAM313; fragment IV, pAM314; fragment V, pAM318. The positions of the Shine-Dalgarno sequence (SD), ATG initiation codon (ATG), and relevant restriction sites are shown.

*E. coli* JA221/F'lacI$^q$ containing each of the mic-(ompA) plasmids was pulse-labeled with [$^{35}$S]-methionine for one minute with and without a one-hour prior preincubation with IPTG. Electrophoretic patterns of the outer membrane proteins isolated from these cultures were obtained. The autoradiographs revealed that each of the five mic(ompA) genes is capable of inhibiting OmpA synthesis. The mic(ompA) genes appear to be less effective than the mic(lpp) and mic(ompC) genes described earlier. However, this problem was circumvented by increasing the mic(ompA) gene dosage.

The plasmid pAM301, encoding an mRNA complementary to a 258 base region of the OmpA mRNA encompassing the translation initiation site (fragment I in FIG. 3) was found to inhibit OmpA synthesis by approximately 45 percent. A similar inhibition was obtained with pAM307, by approximately 51 percent. This plasmid contains fragment II (see FIG. 3) which does not include any DNA sequences corresponding to the ompA structural gene. The inhibition by PAM307 was not surprising because the mic(ompC) experiments described earlier showed that increased complementarity to the 5'-leader region of the mRNA was more effective in micRNA-mediated inhibition. On the other hand, pAM313, which produces a micRNA that is complementary only to the portion of the ompA structural gene covered by fragment III (See FIG. 8) which spans the coding region for amino acid residues 4 through 45 of pro-OmpA, was also effectively able to inhibit OmpA synthesis by approximately 54 percent, indicating that the micRNA does not need to hybridize to the initiation site for protein synthesis and/or to the 5'-leader region of the target mRNA in order to function. This was also confirmed using mic(lpp) genes. Two mic(lpp) RNAs which were complementary to only the coding region of the lpp mRNA have also been found to inhibit lipoprotein production. The effect of the mic(lpp) genes in pJDC413 and pJDC414 which were constructed from the lpp structural gene fragments coding for amino acid residues 3 to 29, and 43 to 63 of prolipoprotein, respectively, were observed. Both pJDC413 and PJDC414, however, exhibit only a 2-fold inhibition of lipoprotein synthesis indicating that a DNA fragment covering the translation initiation site (which caused a 16-fold inhibition) is more effective in the case of the mic(lpp) genes.

Fragment IV (see FIG. 8) was chosen to test the effectiveness of a micRNA complementary only to the 5' leader region of the ompA mRNA The resulting construct pAM314, synthesizes a micRNA complementary to a 68-base stretch of the ompA mRNA leader located 60 bases upstream of the AUG initiation codon. pAM314 exhibits a very weak mic effect, inhibiting OmpA synthesis by only about 18 percent. The significant differences in the mic effect between fragments II and IV (see FIG. 8) clearly demonstrates that the complementary interaction within the region of the mRNA that interacts with the ribosome i.e., the Shine-Dalgarno sequence and/or the coding region, is very important for the effective mic function, although it is not absolutely required. It is also interesting to note that shortening the mic(ompA) gene from fragment I to V had little effect on its efficiency, a 45 percent compared to a 48 percent decrease, respectively.

In order to construct a plasmid capable of inhibiting OmpA synthesis more effectively than those discussed above, plasmids were constructed containing more than one mic(ompA) gene. The plasmid, pAM307 and its derivatives pAM319 and pAM315 were compared. The latter two plasmids contain two and three copies of the mic(ompA) gene in pAM307, respectively. While pAM307 inhibited OmpA synthesis by approximately 47 percent, pAM315 and PAM319 inhibited OmPA synthesis by 69 percent and 73 percent, respectively.

The results presented hereinabove clearly demonstrate that the artificial mic system and techniques of this invention can be used for specifically regulating the expression of a gene of interest. In particular, the inducible mic system for a specific gene is a novel and very effective way to study the function of a gene. If the gene is essential, conditional lethality may be achieved upon the induction of the mic system, somewhat similar to a temperature-sensitive mutation. It should be noted, however, that the mic system blocks the synthesis of the specific protein itself while temperature sensitive mutations block only the function of the protein without blocking its synthesis.

From this invention, the following has become evident:

(a) The production of an RNA transcript (micRNA) that is complementary to a specific mRNA inhibits the expression of that mRNA.

(b) The production of a micRNA specifically blocks the expression of only those genes which share complementarity to the micRNA.

(c) The induction of micRNA production blocks the expression of the specific gene very rapidly in less than the half-life of the mRNA.

(d) The micRNA also reduces the amount of the specific mRNA in the cell, as was found when the natural micF gene was expressed, as well as when the artificially constructed mic(lpp) gene was expressed in the present invention.

(e) There is a clear effect of gene dosage; the more a micRNA is produced, the more effectively the expression of the target gene is blocked.

In the practices of this invention, it appears that regions of the micRNAs that are complementary to regions of the mRNA known to interact with ribosomes are the most effective. Using the lpp gene as an example, it appears that a mic(lpp) RNA that can hybridize to the Shine-Dalgarno sequence and the translation-initiation site of the lpp mRNA inhibits lipoprotein synthesis more efficiently than one which cannot. However, for the ompA gene, micRNAs complementary to both the Shine-Dalgarno sequence and the translation-initiation site, just the Shine-Dalgarno sequence, or the structural gene alone were equally effective.

For some genes, such as ompC and lpp, the region of the gene encompassing the translation-initiation site may not contain a unique sequence, and micRNA induction results in the inhibition of the production of more than one protein. In these cases, another region of the gene may be used to construct the mic gene The length of the micRNA is another variable to be considered. The longer mic(ompC) RNA was 4-fold more effective at inhibiting OmpC production than the shorter mic(ompC) RNA. It should be noted that the inhibition of lipoprotein expression by the mic(ompC) RNA was less effective with the longer mic(ompC) RNA, in spite of the fact that the region of the two mic(ompC) RNAs complementary to the lipoprotein mRNA is the same. This indicates that higher specificity may be achieved by using longer micRNAs. In contrast to the mic(ompC) genes, length did not appear to be a significant factor for the mic(ompA) RNA-mediated inhibition of OmpA production. In addition, the secondary structure of the micRNA most likely plays an important role in micRNA function.

There are several mechanisms by which the micRNA may function to inhibit expression of the specific gene. It is most likely that the micRNA primarily acts by binding to the mRNA, thereby preventing the interaction with ribosomes as proposed earlier. This hypothesis is supported by the fact that the mic(lpp) RNA inhibited lipoprotein production much faster than the time expected if only transcription was affected based on the half-life of the lpp mRNA. Concerning how micRNA causes a reduction in the amount of lipoprotein mRNA, a plausible model to explain this reduction is that the mRNA is less stable when ribosomes are not traversing the entire mRNA.

Another possible model to explain this reduction in mRNA level is that complementary hybrid formation between the micRNA and the mRNA causes premature termination of transcription or destabilization of the mRNA. Alternatively, the micRNA may directly inhibit the initiation of transcription, or cause pausing of mRNA elongation in a manner similar to that described for the function of a small complementary RNA species in ColE1 replication, see Tomizawa et al., "The importance of RNA secondary structure in ColE1 primer formation." Cell 31, 575-583 (1982).

In accordance with the practices of this invention the accompanying disclosure presents a powerful tool and technique for regulating gene expression. Gene expression in accordance with the practices of this invention is regulated by incorporating foreign DNA that associates with the genetic material of an organism (i.e. transformation). The organism may possess only its native genetic material or may have been genetically altered by the deletion of native genetic material or the addition of foreign genetic material. Upon transcription of the DNA of said organism, an oligoribonucleotide or polyribonucleotide RNA is produced. This mRNA is complementary to and/or capable of hybridizing with an mRNA produced by the DNA of the organism so that expression or translation of said mRNA is inhibited or prevented.

Gene expression regulation of an organism in accordance with the practices of this invention is carried out in a transformed organism. Along with the genetic material of said organism there is incorporated non-native DNA which is transcribed along with the DNA of the said organism. Through transcription, the non-native DNA produces mRNA that is complementary to and capable of hybridizing to the mRNA that is produced from the native DNA. Hybridization, thus, inhibits or prevents translation of the mRNA into protein.

In the practices of this invention, the non-native DNA that is transcribed along with the native DNA into mRNA that is complementary to the mRNA produced by the native DNA may be incorporated into the native DNA directly or indirectly. Direct incorporation of the DNA necessitates inserting the DNA directly into the nucleus that contains the organism's DNA. This may be accomplished through microinjection. Indirect incorporation is done through incorporating the non-native DNA into a plasmid or viral vector and then transforming the said organism with the plasmid or viral vector. The plasmid or viral vector may be inserted into the organism through the membrane thereof into the cytoplasm and travel to the nucleus and associate with the DNA that characterizes the organism. Where desired, convenient, or practical, microinjection may be employed to insert the DNA or the plasmid or viral vector containing the DNA insert into the organism into the nucleus or cytoplasm of the organism. It is usually convenient to transform the organism with the DNA or the plasmid or viral vector containing the DNA insert through the membrane that encompasses the organism by known methods, such as, electroporation, coprecipitation or microinjection.

The practices of this invention are generally applicable with respect to any organism containing genetic material which is capable of being expressed. Suitable organisms include the prokaryotic and eukaryotic organisms, such as bacteria, yeast and other cellular organisms. The practices of this invention are also applicable to viruses, particularly where the viruses are incorporated in the organisms.

In its application, the mic system of this invention has great potential to block the expression of various toxic or harmful genes permanently or upon induction. These genes include drug resistance genes, oncogenes, and phage or virus genes among others.

In the development and demonstration of the practices of this invention as described herein, the following materials and procedures were employed.

Strain and Medium

*E. coli* JA221 (hsdr leuB6 lacY thi recA trpE5)F'-(lacI$^q$ proAB lacZYA) was used in all experiments. This strain was grown in M9 medium (J. H. Miller, Experiments in Molecular Genetics. Cold Spring Harbor Laboratory, Cold Spring Harbor, N.Y. (1972)) supplemented with 0.4 percent glucose, 2 μg/ml thiamine, 40 μg/ml each of leucine and tryptophan, and 50 μg/ml ampicillin, unless otherwise indicated.

Materials

Restriction enzymes were purchased from either Bethesda Research Laboratories or New England BioLabs. T4 DNA ligase and *E. coli* DNA polymerase I(large fragment) were purchased from Bethesda Research Laboratories. All enzymes were used in accordance with the instructions provided by the manufacturer. XbaI linkers (CTCTAGAG) were purchased from New England BioLabs.

DNA Manipulation

Plasmids pJDC402, pJDC412, and pJDC422 were constructed as described herein and FIG. 1. Plasmids pJDC413 and pJDC414 were constructed by isolating the 80-bp AluI fragment from the IPP gene encoding amino acid residues 3 through 29 of prolipoprotein for pJDC413 and the 58-bp AluI fragment encoding amino acid residues 43 through 63 of prolipoprotein for pJDC414. The fragments were blunt end ligated into pJDC402 which was first digested with XbaI followed by treatment with DNA polymerase I (large fragment).

The isolation of the appropriate ompC fragments for mic(ompC) construction involved a subcloning step due to the absence of suitable unique restriction sites between the ompC promoter and structural gene. Two derivatives of the ompC containing plasmid, PMY150, lacking either the 471-bp XbaI-MnI ompC promoter containing fragment (pDR001 and PDR002, respectively), but containing an XbaI site in its place, were isolated. The unique BglII sites in each of these plasmids were changed to XbaI sites by treatment with DNA polymerase I (large fragment) and ligation with synthetic XbaI linkers. Following XbaI digestion, the 123-bp XbaI fragment from pDR001 and the 175-bP XbaI fragment from pDR002 were individually isolated and cloned into the XbaI site of pJDC402 to create pAM308 and PAM309, respectively. pAM320 contains the HinfI fragment covering the mic(ompC) gene isolated from pAM308 cloned into the PvuII site of pAM308. pAM321 was similarly constructed from pAM309 to also contain two mic(ompC) genes.

The mic(ompA) plasmids pAM301, PAM307, pAM313, pAM314, and pAM318 were constructed as described in a manner similar to the construction of the mic(lpp) and the mic(ompC) genes. To construct pAM319, the HinfI fragment containing the mic(ompA) gene was isolated from pAM307 and inserted back into the PvuII site of PAM307. pAM315 was constructed in the same manner as pAM319 except that it contains two HinfI fragments inserted into the PvuII site of pAM307.

Analysis of Outer Membrane Protein Production

*E. coli* JA221/F'lacI$^q$ carrying the appropriate plasmid were grown to a Klett-Summerson colorimeter reading of 30, at which time IPTG was added to a final concentration of 2 mM. After one additional hour of growth (approximately one doubling), 50 uCi of [$^{35}$S]-Methionine (Amersham, 1000 Ci/mMole) was added to 1 ml of the culture. The mixture was then incubated with shaking for one minute, at which time the labeling was terminated by addition of 1 ml ice cold stop solution (20 mM sodium phosphate [pH 7.1], containing 1 percent formaldehyde, and 1 mg/ml methionine). Cells were washed once with 10 mM sodium phosphate [pH 7.1], suspended in 1 ml of the same buffer, and sonicated with a Heat Systems Ultrasonics sonicator model W-220E with a cup horn adapter for 3 minutes (in 30 second pulses). Unbroken cells were removed by low speed centrifugation prior to collecting the outer membrane. Cytoplasmic membranes were solubilized during a 30 minute incubation at room temperature in the presence of 0.5 percent sodium lauroyl sarcosinate and the outer membrane fraction was precipitated by centrifugation at 105,000×g for 2 hours.

Lipoprotein and OmpA were analyzed by Tris-SDS polyacrylamide gel electrophoresis (SDS-PAGE). To analyze OmpC production, urea-SDS polyacrylamide gel electrophoresis (urea-SDS-PAGE) was used. Proteins were dissolved in the sample buffer and the solution was incubated in a boiling water bath for 8 minutes prior to gel application. The autoradiographs of dried gels were directly scanned by a Shimadzu densitometer. To determine relative amounts of the band of interest, the ratio of the area of the peak of interest to the area of an unaffected protein peak, was determined for each sample.

RNA Analysis

Cells were grown and labeled with [$^{3}$H]-uridine, then cell growth was stopped by rapidly chilling the culture on ice for less than 5 minutes. The cells were collected by centrifugation at 8000 rpm for 5 minutes. RNA was isolated using the following procedure. The cells were quickly resuspended in hot lysis solution (10 mM Tris-HCl [pH 8.0], 1 mM EDTA, 350 mM NaCl, 2 percent SDS and 7 M urea) with vigorous vortexing for 1 minute. The mixture was immediately extracted, twice with phenol:chloroform (1:1) and twice with chloroform alone. One tenth volume of 3M sodium acetate (pH 5.2) was added to the mixture and 3 volumes of ethanol was added to precipitate the RNA. The precipitate was then dissolved in TE buffer (10 mM Tris-HCl [pH 7.5], 1 mM EDTA). For gel electrophoresis, equal counts were loaded in each lane. The RNA was separated on a 1.5 percent agarose gel containing 6 percent formaldehyde. The running buffer was 20 mM MOPS (3-[N-morpholino]propanesulfonic acid [Sigma]), 5 mM sodium acetate and 1 mM EDTA, pH 7.0.

RNA was transferred to nitrocellulose paper. M13 hybridization probes specific for the mic(lpp) RNA and lpp mRNA were individually constructed by cloning the 112-bp XbaI fragment shown in FIG. 1-B into M13 mp9 in the appropriate orientation. A probe specific for the ompA mRNA was constructed by inserting a 1245-bp XbaI-EcoRI fragment (originally an EcoRV-PSTI fragment) into M13 mp10 and the probes were labeled.

As will be apparent to those skilled in the art in the light of the foregoing disclosure, many modifications, alterations and substitutions are possible in the practices of this invention without departing from the spirit or scope thereof.

What is claimed is:

1. A method of regulating the function of a gene in a cell, comprising introducing into a cell a non-native polynucleotide construct which, when present in said cell, produces a non-naturally occurring polynucleotide complementary to an RNA transcript produced by said gene; whereby said polynucleotide which is complementary to said RNA transcript produced by said gene regulates the function of said gene.

2. The method of regulating the function of a gene in a cell according to claim 1 wherein said non-native polynucleotide construct comprises an inducible promoter and which method further comprises the step of providing to said cell an inducer for inducting said inducible promoter.

3. The method of regulating the function of a gene in a cell according to claim 1 wherein said gene is an oncogene.

4. The method of regulating the function of a gene in a cell according to claim 1 wherein said gene is a viral gene.

5. The method of regulating the function of a gene in a cell according to claim 1 wherein said gene encodes a positive regulator whose presence is necessary for the expression of another gene.

6. The method of regulating the function of a gene in a cell according to claim 1 wherein said gene is related to a genetic disease or defect.

7. The method of regulating the function of a gene in a cell according to claim 1 wherein said gene encodes a protein.

8. The method of regulating the function of a gene in a cell according to claim 7 wherein the polynucleotide produced from the non-native polynucleotide construct is complementary to the coding region of the RNA transcript produced by said gene.

9. The method of regulating the function of a gene in a cell according to claim 7 wherein the polynucleotide produced from the non-native polynucleotide construct is complementary to the non-coding region of the RNA transcript produced by said gene.

10. The method of regulating the function of a gene in a cell according to claim 7 wherein the polynucleotide produced from the non-native polynucleotide construct is complementary to the 5' non-coding region of the RNA transcript produced by said gene.

11. The method of regulating the function of a gene in a cell according to claim 7 wherein the polynucleotide produced from the non-native polynucleotide construct is complementary to the ribosome binding region of the RNA transcript produced by said gene.

12. The method of regulating the function of a gene in a cell according to claim 7 wherein the polynucleotide produced from the non-native polynucleotide construct is complementary to the translation initiation region of the RNA transcript produced by said gene.

13. The method of regulating the function of a gene in a cell according to claim 7 wherein the polynucleotide produced from the non-native polynucleotide construct is complementary to the ribosome binding region and the translation initiation region of the RNA transcript produced by said gene.

14. The method of regulating the function of a gene in a cell according to claim 1 wherein said non-native polynucleotide construct is incorporated into a vector.

15. The method of regulating the function of a gene in a cell according to claim 14 wherein said vector is a plasmid.

16. The method of regulating the function of a gene in a cell according to claim 14 wherein said vector is a viral vector.

17. The method of regulating the function of a gene in a cell according to claim 14 wherein said vector is either single-stranded or double-stranded.

18. The method of claim 1 wherein said cell is prokaryotic.

19. The method of claim 1 wherein said cell is eukaryotic.

20. The method of claim 1 wherein the non-native polynucleotide construct is introduced into the nucleus of said cell.

21. The method of claim 1 wherein the non-native polynucleotide construct is introduced into said cell by microinjection.

22. The method of claim 1 wherein the non-native polynucleotide construct is introduced into said cell by electroporation.

23. The method of claim 1 wherein the non-native polynucleotide construct is introduced into said cell by coprecipitation.

24. The method of any one of claims 1 to 23 wherein said non-native polynucleotide construct is DNA.

25. The method of any one of claims 1 to 23 wherein said non-native polynucleotide construct is RNA.

26. A method of regulating the function of a gene in a cell, comprising the steps of:
   (a) preparing a non-native polynucleotide construct which comprises
      (i) a transcriptional promoter segment and
      (ii) a polynucleotide segment comprising a segment of said gene, with said gene segment operably linked downstream of said promoter segment and being inverted with respect to said promoter segment; and
   (b) introducing said non-native polynucleotide construct into said cell containing said gene;
   whereby transcription of said inverted gene segment regulates the function of said gene.

27. The method of regulating the function of a gene in a cell according to claim 26 wherein said transcriptional promoter segment of said non-native polynucleotide construct comprises an inducible promoter and which method further comprises the step of providing to said cell an inducer for inducing said inducible promoter.

28. The method of regulating the function of a gene in a cell according to claim 26 wherein said gene is an oncogene.

29. The method of regulating the function of a gene in a cell according to claim 26 wherein said gene is a viral gene.

30. The method of regulating the function of a gene in a cell according to claim 26 wherein said gene encodes a positive regulator whose presence is necessary for the expression of another gene.

31. The method of regulating the function of a gene in a cell according to claim 26 wherein said gene is related to a genetic disease or defect.

32. The method of regulating the function of a gene in a cell according to claim 26 wherein said gene encodes a protein.

33. The method of regulating the function of a gene in a cell according to claim 32 wherein said polynucleotide comprising a segment of said gene encodes an RNA transcript complementary to a coding region of the RNA transcript produced by said gene.

34. The method of regulating the function of a gene in a cell according to claim 32 wherein said polynucleotide comprising a segment of said gene encodes an RNA transcript complementary to a non-coding region of the RNA transcript produced by said gene.

35. The method of regulating the function of a gene in a cell according to claim 32 wherein said polynucleotide comprising a segment of said gene encodes an RNA transcript complementary to the 5= non-coding region of the RNA transcript produced by said gene.

36. The method of regulating the function of a gene in a cell according to claim 32 wherein said polynucleotide comprising a segment of said gene encodes an RNA transcript complementary to the ribosome binding region of the RNA transcript produced by said gene.

37. The method of regulating the function of a gene in a cell according to claim 32 wherein said polynucleotide comprising a segment of said gene encodes an RNA transcript complementary to the translation initiation region of the RNA transcript produced by said gene.

38. The method of regulating the function of a gene in a cell according to claim 32 wherein said polynucleotide comprising a segment of said gene encodes an RNA transcript complementary to the ribosome binding region and the translation initiation region of the RNA transcript produced by said gene.

39. The method of regulating the function of a gene in a cell according to claim 26 wherein said non-native polynucleotide construct is incorporated into a vector.

40. The method of regulating the function of a gene in a cell according to claim 39 wherein said vector is a plasmid.

41. The method of regulating the function of a gene in a cell according to claim 39 wherein said vector is a viral vector.

42. The method of regulating the function of a gene in a cell according to claim 39 wherein said vector is either single-stranded or double-stranded.

43. The method of claim 26 wherein said cell is prokaryotic.

44. The method of claim 26 wherein said cell is eukaryotic.

45. The method of claim 26 wherein the non-native polynucleotide construct is introduced into the nucleus of said cell.

46. The method of claim 26 wherein the non-native polynucleotide construct is introduced into said cell by microinjection.

47. The method of claim 26 wherein the non-native polynucleotide construct is introduced into said cell by electroporation.

48. The method of claim 26 wherein the non-native polynucleotide construct is introduced into said cell by coprecipitation.

49. The method of any one of claims 26 to 48 wherein said non-native polynucleotide construct is DNA.

50. A cell comprising a non-native polynucleotide construct which, when present in a cell containing a gene, produces a non-naturally occurring polynucleotide complementary to a RNA transcript produced by said gene, whereby the polynucleotide which is complementary to said RNA transcript produced by said gene regulates the function of said gene.

51. The cell of claim 50 wherein said non-native polynucleotide construct comprises an inducible promoter step.

52. The cell of claim 50 wherein said gene is an oncogene.

53. The cell of claim 50 wherein said gene is a viral gene.

54. The cell of claim 50 wherein said gene encodes a positive regulator whose presence is necessary for the expression of another gene.

55. The cell of claim 50 wherein said gene is related to a genetic disease or defect.

56. The cell of claim 50 therein said gene encodes a protein.

57. The cell of claim 56 wherein the polynucleotide produced from the non-native polynucleotide construct is complementary to the coding region of the RNA transcript produced by said gene.

58. The cell of claim 56 wherein the polynucleotide produced from the non-native polynucleotide construct is complementary to the non-coding region of the RNA transcript produced by said gene.

59. The cell of claim 56 wherein the polynucleotide produced from the non-native polynucleotide construct is complementary to the 5= non-coding region of the RNA transcript produced by said gene.

60. The cell of claim 56 wherein the polynucleotide produced from the non-native polynucleotide construct is complementary to said ribosome binding region of the RNA transcript produced by said gene.

61. The cell of claim 56 wherein the polynucleotide produced from the non-native polynucleotide construct is complementary to the translation initiation region of the RNA transcript produced by said gene.

62. The cell of claim 56 wherein the polynucleotide produced from the non-native polynucleotide construct is complementary to the ribosome binding region and the translation initiation region of said RNA transcript produced by said gene.

63. The cell of claim 56 wherein the non-native polynucleotide construct is incorporated into a vector.

64. The cell of claim 63 wherein said vector is a plasmid.

65. The cell of claim 63 wherein said vector is a viral vector.

66. The cell of claim 63 wherein said vector is either single-stranded or double-stranded.

67. The cell of claim 50 wherein said cell is prokaryotic.

68. The cell of claim 50 wherein said cell is eukaryotic.

69. The cell of claim 50 wherein the non-native polynucleotide construct is introduced into the nucleus of said cell.

70. The cell of claim 50 wherein the non-native polynucleotide construct is introduced into said cell by microinjection.

71. The cell of claim 50 wherein the non-native polynucleotide construct is introduced into said cell by electroporation.

72. The cell of claim 50 wherein the non-native polynucleotide construct is introduced into said cell by co-precipitation.

73. A cell comprising a non-native polynucleotide construct which, when present in a cell containing a gene, regulates the function of said gene, said non-native polynucleotide construct comprising:
  (a) a transcriptional promoter segment and
  (b) a polynucleotide segment comprising a segment of said gene, with said gene segment operably linked downstream of said promoter segment and being inverted with respect to said promoter segment;
whereby transcription of said inverted gene segment regulates the function of said gene.

74. The cell of claim 73 wherein said transcriptional promoter segment of said non-native polynucleotide construct comprises an inducible promoter.

75. The cell of claim 73 wherein said gene is an oncogene.

76. The cell of claim 73 wherein said gene is a viral gene.

77. The cell of claim 73 wherein said gene encodes a positive regulator whose presence is necessary for the expression of another gene.

78. The cell of claim 73 wherein said gene is related to a genetic disease or defect.

79. The cell of claim 73 wherein said gene encodes a protein.

80. The cell of claim 79 wherein said polynucleotide comprising a segment of said gene encodes an RNA transcript complementary to the coding region of the RNA transcript produced by said gene.

81. The cell of claim 79 wherein said polynucleotide comprising a segment of said gene encodes an RNA transcript complementary to the non-coding region of the RNA transcript produced by said gene.

82. The cell of claim 79 wherein said polynucleotide comprising a segment of said gene encodes an RNA transcript complementary to the 5' non-coding region of the RNA transcript produced by said gene.

83. The cell of claim 79 wherein said polynucleotide comprising the segment of said gene encodes an RNA transcript complementary to the ribosome binding region of the RNA transcript produced by said gene.

84. The cell of claim 79 wherein said polynucleotide comprising a segment of said gene encodes an RNA transcript complementary to the translation initiation region of the RNA transcript produced by said gene.

85. The cell of claim 79 wherein said polynucleotide comprising the segment of said gene encodes an RNA transcript complementary to the ribosome binding region and the translation initiation region of the RNA transcript produced by said gene.

86. The cell of claim 73 wherein said non-native polynucleotide construct is incorporated into a vector.

87. The cell of claim 86 wherein said vector is a plasmid.

88. The cell of claim 86 wherein said vector is a viral vector.

89. The cell of claim 86 wherein said vector is either single-stranded or double-stranded.

90. The cell of claim 73 wherein said cell is prokaryotic.

91. The cell of claim 73 wherein said cell is eukaryotic.

92. The cell of claim 73 wherein said non-native polynucleotide construct is introduced into the nucleus of said cell.

93. The cell of claim 73 wherein said non-native polynucleotide construct is introduced into said cell by microinjection.

94. The cell of claim 73 wherein said non-native polynucleotide construct is introduced into said cell by electroporation.

95. The cell of claim 73 wherein said non-native polynucleotide construct is introduced into said cell by co-precipitation.

96. A non-native polynucleotide construct which, when present in a cell containing a gene, produces a non-naturally occurring polynucleotide complementary to a RNA transcript produced by said gene, whereby the polynucleotide which is complementary to said RNA transcript produced by said gene regulates the function of said gene.

97. The construct of claim 96 wherein said non-native polynucleotide construct comprises an inducible promoter.

98. The construct of claim 96 wherein said gene is an oncogene.

99. The construct of claim 96 wherein said gene is a viral gene.

100. The construct of claim 96 wherein said gene encodes a positive regulator whose presence is necessary for the expression of another gene.

101. The construct of claim 96 wherein said gene is related to a genetic disease or defect.

102. The construct of claim 96 wherein said gene encodes a protein.

103. The construct of claim 102 wherein the polynucleotide produced from the non-native polynucleotide construct is complementary to the coding region of the RNA transcript produced by said gene.

104. The construct of claim 102 wherein the polynucleotide produced from the non-native polynucleotide construct is complementary to the non-coding region of the RNA transcript produced by said gene.

105. The construct of claim 102 wherein the polynucleotide produced from the non-native polynucleotide construct is complementary to the 5' non-coding region of the RNA transcript produced by said gene.

106. The construct of claim 102 wherein the polynucleotide produced from the non-native polynucleotide construct is complementary to the ribosome binding region of the RNA transcript produced by said gene.

107. The construct of claim 102 wherein the polynucleotide produced from the non-native polynucleotide construct is complementary to the translation initiation region of the RNA transcript produced by said gene.

108. The construct of claim 102 wherein the polynucleotide produced from the non-native polynucleotide construct is complementary to the ribosome binding region and the translation initiation region of said RNA transcript produced by said gene.

109. The construct of claim 96 wherein the non-native polynucleotide construct is incorporated into a vector.

110. The construct of claim 109 wherein said vector is a plasmid.

111. The construct of claim 109 wherein said vector is a viral vector.

112. The construct of claim 109 wherein said vector is either single-stranded or double-stranded.

113. The construct of claim 96 wherein said cell is prokaryotic.

114. The construct of claim 96 wherein said cell is eukaryotic.

115. The construct of claim 96 wherein the non-native polynucleotide construct is introduced into the nucleus of said cell.

116. The construct of claim 96 wherein the non-native polynucleotide construct is introduced into said cell by microinjection.

117. The construct of claim 96 wherein the non-native polynucleotide construct is introduced into said cell by electroporation.

118. The construct of claim 96 wherein the non-native polynucleotide construct is introduced into said cell by coprecipitation.

119. The construct any one of claims 96–118 wherein said non-native polynucleotide construct is DNA.

120. A pharmaceutical composition which comprises the polynucleotide construct of any one of claims 96–118.

121. A method of regulating the function of a gene in a cell which comprises:
   introducing into said cell the polynucleotide construct of any one of claims 96 to 118 whereby a transformed cell is obtained; and
   growing said transformed cell whereby the polynucleotide which is complementary to said RNA transcript produced by said gene regulates the functioning of said gene.

122. A non-native polynucleotide construct which, when present in a cell containing a gene, regulates the function of said gene, said non-native polynucleotide construct comprising:
   (a) a transcriptional promoter segment and
   (b) a polynucleotide segment comprising a segment of said gene, with said gene segment operably linked downstream of said promoter segment and being inverted with respect to said promoter segment;
   whereby transcription of said inverted gene segment regulates the function of said gene.

123. The non-native polynucleotide construct of claim 122 wherein said transcriptional promoter segment of said non-native polynucleotide construct comprises an inducible promoter.

124. The non-native polynucleotide construct of claim 122 wherein said gene is an oncogene.

125. The non-native polynucleotide construct of claim 122 wherein said gene is a viral gene.

126. The non-native polynucleotide construct of claim 122 wherein said gene encodes a positive regulator whose presence is necessary for the expression of another gene.

127. The non-native polynucleotide construct of claim 122 wherein said gene is related to a genetic disease or defect.

128. The non-native polynucleotide construct of claim 122 wherein said gene encodes a protein.

129. The non-native polynucleotide construct of claim 128 wherein said polynucleotide comprising a segment of said gene encodes an RNA transcript complementary to a coding region of an RNA transcript produced by said gene.

130. The non-native polynucleotide construct of claim 128 wherein said polynucleotide comprising a segment of said gene encodes an RNA transcript complementary to the non-coding region of an RNA transcript produced by said gene.

131. The non-native polynucleotide construct of claim 128 wherein said polynucleotide comprising a segment of said gene encodes an RNA transcript complementary to the 5' non-coding region of the RNA transcript produced by said gene.

132. The non-native polynucleotide construct of claim 128 wherein said polynucleotide comprising a segment of said gene encodes an RNA transcript complementary to the ribosome binding region of the RNA transcript produced by said gene.

133. The non-native polynucleotide construct of claim 128 wherein said polynucleotide comprising a segment of said gene encodes an RNA transcript complementary to the translation initiation region of the RNA transcript produced by said gene.

134. The non-native polynucleotide construct of claim 128 wherein said polynucleotide comprising a segment of said gene encodes an RNA transcript complementary to the ribosome binding region and the translation initiation region of the RNA transcript produced by said gene.

135. The non-native polynucleotide construct of claim 122 wherein said non-native polynucleotide construct is incorporated into a vector.

136. The non-native polynucleotide construct of claim 135 wherein said vector is a plasmid.

137. The non-native polynucleotide construct of claim 135 wherein said vector is a viral vector.

138. The non-native polynucleotide construct of claim 135 wherein said vector is either single-stranded or double-stranded.

139. The non-native polynucleotide construct of claim 122 wherein said cell is prokaryotic.

140. The non-native polynucleotide construct of claim 122 wherein said cell is eukaryotic.

141. The non-native polynucleotide construct of claim 122 wherein said non-native polynucleotide construct is introduced into the nucleus of said cell.

142. The non-native polynucleotide construct of claim 122 wherein said non-native polynucleotide construct is introduced into said cell by microinjection.

143. The non-native polynucleotide construct of claim 122 wherein said non-native polynucleotide construct is introduced into said cell by electroporation.

144. The non-native polynucleotide construct of claim 122 wherein said non-native polynucleotide construct is introduced into said cell by coprecipitation.

145. The construct of any one of claims 122 to 144 wherein said non-native polynucleotide construct is a DNA construct.

146. A pharmaceutical composition which comprises the polynucleotide construct of any one of claims 122 to 144.

147. A method of regulating the function of a gene in a cell which comprises:
   introducing into said cell the polynucleotide construct of any one of claims 122 to 146 whereby the transformed cell is obtained; and
   growing said transformed cell whereby the RNA produced by transcription of the inverted gene segment regulates the functioning of said gene.

* * * * *